(12) United States Patent
Jackson, III et al.

(10) Patent No.: US 11,576,703 B2
(45) Date of Patent: Feb. 14, 2023

(54) IMPLANTABLE MODULAR ORTHOPEDIC PLATE SYSTEM

(71) Applicant: FREEDOM INNOVATIONS, LLC, Grand Blanc, MI (US)

(72) Inventors: Avery M. Jackson, III, Grand Blanc, MI (US); John Souza, Sr., Monroe, NC (US)

(73) Assignee: FREEDOM INNOVATIONS, LLC, Grand Blanc, MI (US)

( * ) Notice: Subject to any disclaimer, the term of this patent is extended or adjusted under 35 U.S.C. 154(b) by 32 days.

(21) Appl. No.: 17/093,093

(22) Filed: Nov. 9, 2020

(65) Prior Publication Data

US 2021/0137573 A1    May 13, 2021

Related U.S. Application Data

(60) Provisional application No. 62/932,380, filed on Nov. 7, 2019.

(51) Int. Cl.
*A61B 17/70* (2006.01)
*A61B 17/80* (2006.01)
*A61B 17/00* (2006.01)

(52) U.S. Cl.
CPC .......... *A61B 17/7059* (2013.01); *A61B 17/80* (2013.01); *A61B 17/8023* (2013.01); *A61B 2017/00477* (2013.01)

(58) Field of Classification Search
CPC ................ A61B 17/7059; A61B 17/80; A61B 17/8023
See application file for complete search history.

(56) References Cited

U.S. PATENT DOCUMENTS

| | | |
|---|---|---|
| D376,971 S | 12/1996 | Schutz |
| 5,843,082 A | 12/1998 | Yuan et al. |
| 6,602,256 B1 | 8/2003 | Hayes |
| 6,645,208 B2 | 11/2003 | Apfelbaum et al. |
| 6,878,167 B2 | 4/2005 | Ferree |

(Continued)

OTHER PUBLICATIONS

Notification of Transmittal of the International Search Report and the Written Opinion of the International Searching Authority, or the Declaration for corresponding International Application No. PCT/US17/28457; filed Apr. 19, 2017.

*Primary Examiner* — Larry E Waggle, Jr.
(74) *Attorney, Agent, or Firm* — McNees Wallace & Nurick LLC

(57) ABSTRACT

An implantable modular plate system for stabilizing adjacent vertebral bodies in a cervical spine includes at least two plate segments aligned or connected together so as to form a connection at and along adjacent ends. At least one of the plate segments includes a flange at an engagement end and at least one of the plate segments including a flange recess at an engagement end, the flange being configured for overlay engagement with the flange recess when the at least two plate segments are engaged. The plate segments are pivotable out of plane with one another at a common axis of rotation traversing overlapping portions of the adjacent ends and are constrained from rotation by the flanges such that the rotation of each plate segment is limited to up to 90 degrees of rotation away from the contact surfaces of the flange and flange recess.

20 Claims, 14 Drawing Sheets

(56) References Cited

U.S. PATENT DOCUMENTS

| | | | |
|---|---|---|---|
| 7,041,105 B2 * | 5/2006 | Michelson | A61B 17/8019 |
| | | | 606/247 |
| 7,547,306 B2 | 6/2009 | Michelson | |
| 8,172,191 B1 | 5/2012 | Zimbalatti | |
| 8,257,355 B2 * | 9/2012 | Chin | A61B 17/7059 |
| | | | 606/284 |
| 8,262,710 B2 | 9/2012 | Freedman et al. | |
| 8,814,869 B2 | 8/2014 | Freid et al. | |
| 10,363,072 B2 | 7/2019 | Bauerle et al. | |
| 10,828,071 B2 | 11/2020 | Jackson | |
| 2002/0151896 A1 | 10/2002 | Ferree | |
| 2003/0229348 A1 | 12/2003 | Sevrain | |
| 2006/0089648 A1 | 4/2006 | Masini | |
| 2006/0271052 A1 | 11/2006 | Stern | |
| 2006/0276794 A1 | 12/2006 | Stern | |
| 2007/0293865 A1 | 12/2007 | Ko | |
| 2008/0033438 A1 * | 2/2008 | Frizzell | A61F 2/44 |
| | | | 606/104 |
| 2008/0161861 A1 | 7/2008 | Huebner | |
| 2008/0195158 A1 | 8/2008 | De Villiers | |
| 2008/0244866 A1 | 10/2008 | Stanley | |
| 2009/0043341 A1 | 2/2009 | Tyber et al. | |
| 2009/0163960 A1 | 6/2009 | Binder et al. | |
| 2009/0326589 A1 | 12/2009 | Lemoine et al. | |
| 2013/0060288 A1 | 3/2013 | Rodgers et al. | |
| 2013/0173004 A1 | 7/2013 | Greenhalgh et al. | |
| 2013/0310650 A1 | 11/2013 | Hales | |
| 2015/0173812 A1 | 6/2015 | Masson | |
| 2015/0366595 A1 | 12/2015 | Kaufmann et al. | |
| 2016/0000482 A1 | 1/2016 | Ehmke et al. | |
| 2016/0066969 A1 | 3/2016 | Reuter | |
| 2018/0235671 A1 * | 8/2018 | Jackson, III | A61F 2/4455 |
| 2019/0388126 A1 | 12/2019 | Sheffer et al. | |
| 2020/0015863 A1 | 1/2020 | Ganter et al. | |

* cited by examiner

IMPLANTABLE MODULAR ORTHOPEDIC PLATE SYSTEM

PRIORITY CLAIM

This application claims the benefit under 35 U.S.C. § 119(e) to U.S. Provisional Application Ser. No. 62/932,380 filed Nov. 7, 2019, the entirety of which application is incorporated herein by reference.

TECHNICAL FIELD

This invention relates to an implantable plate system for fixation to bones. An embodiment of the invention relates to an implantable plate system for spinal fixation. The implantable plate system may be affixed to bone using any suitable surgical procedure, and in some embodiments for the spine, the implantable plate system may be implanted via an anterior procedure. The implantable plate system may be used together with one or more other devices, for example, spinal implants that fuse vertebrae together.

BACKGROUND

The cervical spine comprises seven cervical vertebrae named by their position in order from C1 adjacent the skull to C7 adjacent the thoracic spine. The C1 vertebra supports the skull and is named the atlas. The C2 vertebra is named the axis and provides the axis upon which the skull and atlas rotate when the head is moved side to side. Intervertebral discs are located between adjacent vertebra except the first two cervical vertebrae, C1 and C2. Motion between adjacent vertebrae occurs through the disc and two facet joints.

As people age the discs lose some of their water content and consequently some of their shock absorbing ability. Tears may form without symptoms in the outer ring or annulus of the disc and heal by forming scar tissue. Scar tissue is weaker than normal tissue, and as the disc continues to wear it begins to collapse and the space between adjacent vertebrae becomes smaller, affecting alignment of the facet joints in the back of the spine. The change in the way the bones fit together causes abnormal pressure on the articular cartilage, and over time this abnormal pressure causes wear and tear arthritis (osteoarthritis) of the facet joints.

Other disorders include spinal disc herniation, fractured or dislocated vertebrae, spinal stenosis, and cervical spondylotic myelopathy. Most neck pain is due to degenerative changes. Perhaps the most serious of the problems caused by degeneration of the spinal segments in the cervical spine is the condition of spinal stenosis, which typically occurs during the later stages of spinal degeneration. In the cervical spine this condition is sometimes called cervical myelopathy.

In cervical spinal stenosis, the spinal canal narrows and can squeeze and compress the nerve roots where they leave the spinal cord, or the spinal cord itself may be compressed. Spinal stenosis is most common in people older than age 50. The aging process can cause a bulging of the discs or a thickening of tissues that connect bones. These disorders can result in nerve compression, leading to paralysis, numbness, or pain.

The vast majority of patients who have neck pain will not require any type of operation. However, in some cases degenerative changes in the cervical spine can lead to a very serious condition where there is too much pressure on the spinal cord. When this condition occurs, the entire spinal cord is in danger.

One surgical option is to remove the pressure on the spinal cord by removing the offending disc or discs, called a discectomy, and to place a bone graft in the space left by removal of the disc. A fusion surgery is almost always done at the same time as the discectomy in order to stabilize the cervical segments. Together, the combined surgery is commonly referred to as an ACDF surgery, which stands for Anterior Cervical Discectomy and Fusion. It may be done for one level or for more than one level of the cervical spine. While this surgery is most commonly done to treat a symptomatic cervical herniated disc, it may also be done for other cervical degenerative diseases.

In the case of a degenerative vertebra, the degenerative vertebra or vertebrae are removed and replaced with a bone graft to fill the space left by removal of the degenerative vertebra. This procedure is called a corpectomy and strut graft. Any bone spurs pushing on the spinal cord are also removed during a corpectomy procedure. A corpectomy is often performed in association with some form of discectomy. In either case, the graft heals over time to create a spinal fusion where the disc or vertebral body has been removed.

Although the cervical spine can be approached from either the front (anterior approach) or from the back (posterior approach), the discs are more directly accessible from the front of the neck and if conditions permit, most surgeons favor an anterior approach. An anterior approach results in less disruption of the normal musculature and it is also easier to maintain the normal alignment of the spine. Many degenerative conditions of the spine cause a loss of the normal lordosis (gentle curvature of the spine). By opening up the front of the spine in an anterior approach, this lordosis can be reestablished.

The anterior approach provides better access to the spine because almost the entire cervical spine is accessible. It provides access to the spine through a relatively uncomplicated pathway, and there generally is less postoperative pain. In a discectomy, the discs can be reached without disturbing the spinal cord, spinal nerves, and neck muscles. All things being equal, the patient tends to have less incisional pain from this approach than from a posterior operation. Depending on the particular symptoms, one disc (single-level) or multiple discs (multi-level) may be removed.

In performing anterior fusion surgery on the cervical spine, a cut is made either transversely or longitudinally in the front of the patient's neck, depending upon the surgeon's training and the levels of surgical fusion. A transverse incision can be made when a one or two level fusion is to be made. When more than a two level fusion is to be made, a longitudinal incision is generally required. The incision length depends on the size of the person and the number of levels to be treated.

In accordance with one procedure for anterior access to the cervical spine, a transverse incision 2-4 centimeters long, depending on the size of the patient and the number of levels, is made just off the midline in the front of the neck, and the cervical fascia is gently divided in a natural plane, between the esophagus and carotid sheath. Small retractors and an operating microscope are used to allow the surgeon to visualize the anterior vertebral body and discs. The arteries and nerves in the neck are protected while the muscles and other tissues are moved to the side.

After the spinal cord and nerve roots have been decompressed at the appropriate levels, the portions removed must be reconstructed so as to support the normal loads of the cervical spine by inserting either a bone graft within each disc space, or inserting a longer graft, referred to as a strut graft, to span the space left by removing one or more vertebral bodies. The intent is to promote the formation of a living bridge of bone between the vertebrae above and below the space formed by removal of one or more vertebrae. The patient's own bone or human cadaver bone may be used to form the graft, or a synthetic scaffold may be used into which bone graft is inserted.

Plating systems have been developed in the prior art to fixedly connect two or more vertebrae to each other and stabilize the cervical spine while the fusion heals. These plating systems typically comprise plates made of titanium and designed to be secured with screws to the vertebrae above and below the fusion. A plate spans the gap between two adjacent vertebrae, and the screws go through holes in the plate and into the vertebrae. Each vertebra may receive one screw or two or more screws depending on the type of plate which is utilized.

The plate system can span one level, i.e. the space between two adjacent vertebrae, or two levels, i.e. the spaces between three adjacent vertebrae, or more levels depending upon the requirements for treating a particular disorder. Once the fusion bone and cervical plate are in place, the vertebrae are stabilized and the bony fusion occurs according to biological healing principles.

Conventional plates are either pre-assembled by the manufacturer into multiple level options, or the plate is assembled by the surgical scrub technicians on the back table then handed to the surgeon for insertion. Plates are usually provided in sets having a range of sizes so as to provide for such features as biological diversity in size, the numbers of segments to be joined, and the length of the portions of bone to be joined. Plating systems are typically designed for joining from two to five vertebrae.

To place the cervical plates, the tissue in front of the vertebrae must be moved to one side to expose the vertebrae. This involves moving the larynx, the pharynx, the esophagus, carotid artery, several important nerves, and dissecting several muscles. Swallowing issues can arise after surgery, particularly when multiple levels are involved, due to the trauma caused when placing a long rigid plate in a small opening with anatomic structures in close proximity. Forcing a large plate for a multi-level fusion into a smaller opening could lead to a dysfunction in esophageal motility, which can affect the swallowing mechanism and the voice.

After gaining access to the prevertebral space and performing the discectomy and fusion, an anterior plate sized to span the number of levels involved, e.g. connecting two motion two vertebrae or one motion segment, is selected. The plate is then placed with fingers or forceps onto the anterior vertebral body surface and screws are inserted through the plate and into the vertebrae to secure the plate to the vertebrae.

It can be extremely difficult to safely place longer multi-level plates into the resection bed because it is difficult to safely retract the soft tissues that must be moved out of the way to place the longer plate for multilevel constructs. There is a potential for resultant esophageal tear or stretch injuries and a risk of causing dysphagia, especially with retraction of the cephalad oropharyngeal tissues when placing the plate. The plate is usually larger than the surgical dissection and requires extra retraction or soft tissue manipulation. Traversing venous or arterial structures are also at risk when placing longer plates. Swallowing dysfunction of some degree is likely. A hoarse voice from injury to the laryngeal nerve or superior thyroid nerve may occur during plate placement and manipulation.

One known complication arising from anterior cervical fusion with conventional plating systems is injury to the esophagus. The risk goes up as the dimensions of the plate increase. Injury to the esophagus can result during surgery when a large, rigid prior art plating system is forced into position through the surgical wound, leading to erosion through the esophagus.

There remains a need for a plate system that can be used in single and in particular in multi-level fusion surgery that enables placement of the plate system without causing excessive soft tissue damage. In particular, what is needed is a plate system that enables sequential placement of plate components with minimal trauma to soft tissue. Further what is needed is a plate system that enables revision surgery to expand the plate system to address adjacent levels.

SUMMARY OF THE INVENTION

The present invention is an implantable modular orthopedic plate system that includes two or more discrete plate segments that inter-engage. In some embodiments, the discrete segments engage by one or more of engagement features, for example keyed interfitting parts, tongue in groove fittings, and hinges. The implantable modular orthopedic plate system is adapted for sequential deployment of each of the discrete plate segments on bone is adapted to minimize trauma to soft tissue. The implantable modular orthopedic plate system provides an extended length plating system that avoids the need to force a large plate into the smaller soft tissue space. The implantable modular orthopedic plate system is particularly useful in the spine, and more particularly, the cervical spine, where space is extremely limited and the use of plates that are designed to traverse two or more levels presents challenges for placement on the anterior spine while preserving soft tissue integrity.

In use, the implantable modular orthopedic plate system may be provided into the surgical field as a pre-assembled set of at least two plate segments that are hingedly connected in an end to end arrangement and in a fully or partially folded configuration. In other embodiments, the implantable modular orthopedic plate system may be provided into the surgical field as separate plate segments that are individually placed, in sequence, and may be hingedly connected to one another prior to or after placement.

The implantable modular orthopedic plate system of the invention includes a set of two or more plate segments (a plurality of plate segments). The plate segments are generally planar and generally square or rectangular in shape, and are adapted to be connected in an end to end configuration. According to embodiments suitable for use in the spine, at least two of the plate segments in the set each spans a single level (i.e., each plate is configured such that its ends can be placed over adjacent vertebrae and the plate spans the disc space therebetween). One or more plate in the set may have at least one engagement end that is one of squared, radiused or lobed at its corners. At least two of the plate segments in the set engage by an overlay of at least a portion of their engagement ends. Thus, each plate includes at one or both ends a surface suitable for overlay engagement with an adjacent plate. The overlaid portions provide reinforcement that resists static and dynamic bending of the plate and provides the advantage of modularity to minimize the overall length of an implant as it is inserted into contact with bone to thereby limit damage to soft tissue.

Each of the plate segments that engage with an adjacent plate segments by flanges may be arranged or folded around a pivot axis and are constrained from rotation by the flanges such that the rotation of each plate segment is limited to up to 90 degrees of rotation away from the contact surfaces of the flange. Thus, each of the two or more plate segments inter-engage by at least overlay interfitting and may also be hingedly connectible. According to such embodiments, two or more plate segments may be connectible by hinged engagement. Hinged engagement of plate segments may be achieved by fixed hinges and releasable hinges. In some embodiments, the fixed hinges comprise one or a plurality of receiving channels on the engagement ends of the plate segments and an engagement pin for fixing them together. In other embodiments, the releasable hinges comprise one or a plurality of engagable arcuate flanges on the engagement ends of adjacent plate segments.

Provided in various embodiments is an implantable modular orthopedic plate system, comprising: at least two plate segments, each plate segment including a top surface, a bottom surface, and first and second ends, wherein at least one end of each of the plate segments is an engagement end for engagement with an adjacent plate segment, the plate segments being connectible together at and along adjacent engagement ends; an access aperture in each of said at least two plate segments, each access aperture arranged and disposed for visualization through the plate segment; a plurality of securement holes through each of said at least two plate segments for receiving screws inserted therethrough; at least one of the at least two plate segments including at its engagement end a flange suitable for overlay engagement with a flange seat on the engagement end of an adjacent plate segment, wherein one of the at least two plate segments includes a flange and one of the least two plate segments includes a flange recess for receiving the flange, each of the flange and the flange recess comprising at least one securement hole, wherein the flange and flange recess securement holes are aligned when the flange is contacted with the flange recess.

In some embodiments an implantable modular plate system for stabilizing adjacent vertebral bodies in a cervical spine comprises: at least two plate segments aligned or connected together so as to form a connection at and along adjacent ends, at least one of the at least two plate segments including a flange at an engagement end and at least one of the at least two plate segments including a flange recess at an engagement end, the flange being configured for overlay engagement with the flange recess when the at least two plate segments are engaged, such that the at least two plate segments are pivotable out of plane with one another at a common axis of rotation traversing overlapping portions of the adjacent ends and are constrained from rotation by the flanges such that the rotation of each plate segment is limited to up to 90 degrees of rotation away from the contact surfaces of the flange and flange recess, and each of the flange and the flange recess comprising at least one securement hole, wherein the flange and flange recess securement holes are aligned when the flange is contacted with the flange recess; an access aperture in each said plate segment arranged and disposed for visualization of an underlying graft site; and a plurality of securement holes through each plate segment for receiving screws inserted therethrough.

In some embodiments an implantable modular orthopedic plate system, comprises: at least two plate segments, each plate segment including a top surface, a bottom surface, and first and second ends, the plate segments being connectible together at and along adjacent engagement ends, wherein each of the said at least two plate segments comprises two engagement ends, each engagement end for engagement with an engagement end of an adjacent plate segment, wherein at least one of the engagement ends on at least two of the said at least two plate segments comprises one of a flange, or a flange recess; an access aperture in each of said at least two plate segments, each access aperture arranged and disposed for visualization through the plate segment; and a plurality of securement holes through each of said at least two plate segments for receiving screws inserted therethrough; at least one of the at least two plate segments including at an engagement end a flange that is oriented adjacent at another of said at least two plate segments including a flange recess at its adjacent engagement end, each of the flange and the flange recess comprising at least one securement hole, wherein the flange and flange recess securement holes are aligned when the flange is contacted with the flange recess.

BRIEF DESCRIPTION OF THE DRAWINGS

The foregoing as well as other objects and advantages of the invention will become apparent from the following detailed description when considered in conjunction with the accompanying drawings, wherein like reference characters designate like parts throughout the several views, and wherein.

KEY to reference numerals in the drawings.

Figure 1:
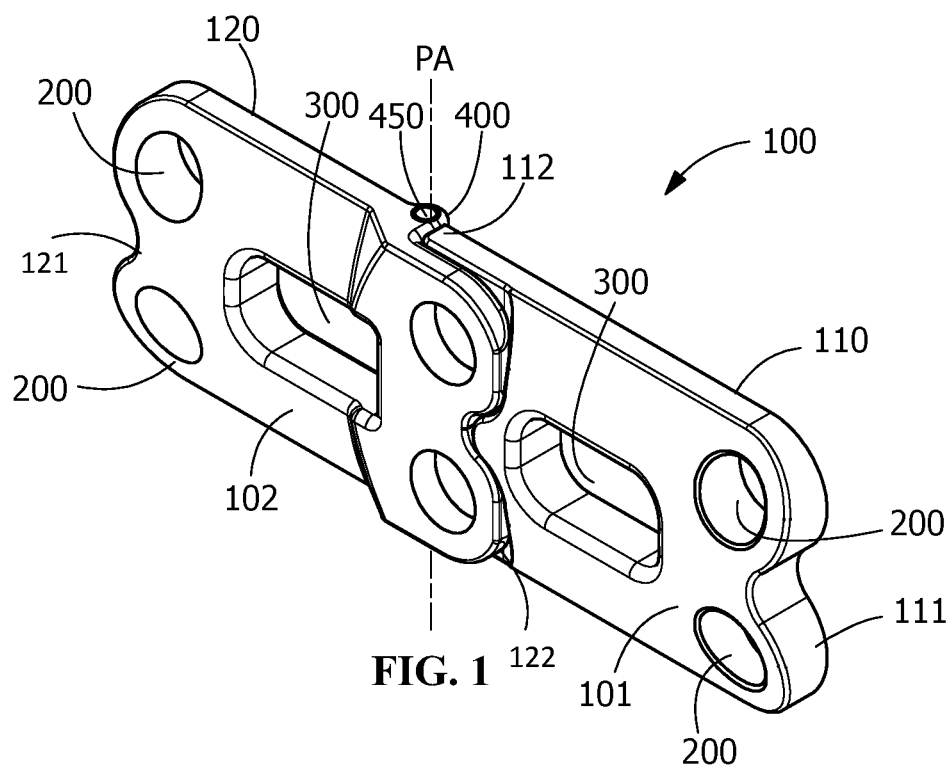
FIG. 1 is a front perspective view of an implantable modular orthopedic plate system according to the disclosure.

| | |
|---|---|
| 100 | Implantable Modular Orthopedic Plate System |
| 101 | Upper Surface (Base) |
| 102 | Upper Surface (Extension) |
| 103 | Lower Surface (Base) |
| 104 | Lower Surface (Extension) |
| 110 | Base Plate |
| 111 | Free End (Base) |
| 112 | Engagement End (Base) |
| 113 | Male Key |
| 114 | Flange Recess |
| 120 | Extension Plate |
| 121 | Free End (Extension) |
| 122 | Engagement End (Extension) |
| 123 | Female Key |
| 124 | Flange |
| 125 | Flange Back |
| 200 | Securement Hole |
| 300 | Access Aperture |
| 400 | Hinge |
| 410 | Center Digit |
| 420 | Outer Digit |
| 430 | Center Digit Receiver |
| 440 | Outer Digit Receiver |
| 450 | Pin |
| 455 | Short Pin |
| 500 | Alternate Plate System |
| 501 | Upper Surface (Base) |
| 502 | Upper Surface (Extension) |
| 503 | Lower Surface (Base) |
| 504 | Lower Surface (Extension) |
| 510 | Base Plate |
| 511 | Free End (Base) |
| 512 | Engagement End (Base) |
| 513 | Male Key |
| 514 | Flange Recess |
| 518 | Tongue |
| 520 | Extension Plate |
| 522 | Free End (Extension) |
| 521 | Engagement End (Extension) |
| 523 | Female Key |
| 524 | Flange |
| 525 | Flange Back |
| 528 | Groove |
| 600 | Alternate Plate System |
| 601 | Upper Surface (Base) |
| 602 | Upper Surface (Extension) |
| 603 | Lower Surface (Base) |
| 604 | Lower Surface (Extension) |
| 610 | Base Plate |
| 611 | Free End (Base) |
| 612 | Engagement End (Base) |
| 613 | Male Key |
| 614 | Flange Recess |
| 615 | Retainer Groove |
| 618 | Retainer Tongue |
| 620 | Extension Plate |
| 622 | Free End (Extension) |
| 621 | Engagement End (Extension) |
| 623 | Female Key |
| 624 | Flange |
| 625 | Flange Back |
| 626 | Extension Groove |
| 628 | Extension Tongue |
| 700 | Alternate Plate System |
| 701 | Upper Surface (Base) |
| 702 | Upper Surface (Extension) |
| 703 | Lower Surface (Base) |
| 704 | Lower Surface (Extension) |
| 710 | Base Plate |
| 711 | Free End (Base) |
| 712 | Engagement End (Base) |
| 713 | Male Key |
| 714 | Contact Recess |
| 715 | Retainer Groove |
| 718 | Retainer Tongue |
| 720 | Extension Plate |
| 722 | Free End (Extension) |
| 721 | Engagement End (Extension) |
| 723 | Female Key |
| 725 | Contact Back Surface |
| 726 | Extension Groove |
| 728 | Extension Tongue |
| 800 | Alternate Plate System |
| 810 | Flange Recess |
| 812 | Insert Abutment |
| 813 | Male Key |
| 815 | Groove |
| 818 | Retainer Tongue |
| 820 | Insert |
| 822 | Insert Upper Surface |
| 823 | Female Key |
| 824 | Insert Back Surface |
| 826 | Insert Edge |
| 900 | Alternate Plate |
| 1000 | Alternate Plate System |
| 1014 | Flange Recess |
| 1015 | Groove |
| 1018 | Retainer Tongue |
| 1025 | Back |
| 1028 | Tongue |
| 2000 | Alternate Plate System |
| 2100 | Base Plate |
| 2111 | Engagement End |
| 2112 | Free End |
| 2114 | Flange Recess |

-continued

| | |
|---|---|
| 2140 | Inner Digit Receiver |
| 2200 | First Extension Plate |
| 2211 | First Engagement End |
| 2212 | Second Engagement End |
| 2214 | Flange Recess |
| 2224 | Flange |
| 2225 | Flange Back |
| 2220 | Outer Digit Receiver |
| 2240 | Inner Digit Receiver |
| 2300 | Second Extension Plate |
| 2311 | First Engagement End |
| 2312 | Second Engagement End |
| 2324 | Flange |
| 2325 | Flange Back |
| 2320 | Outer Digit Receiver |
| 2400 | Linker Plate |
| 2420 | Outer Digit Receiver |
| 2440 | Inner Digit Receiver |
| 2500 | Terminal Extension Plate |
| 2511 | Free End |
| 2512 | Engagement End |
| 2514 | Flange Recess |
| 2524 | Flange |
| 2525 | Flange Back |
| 2520 | Outer Digit Receiver |

DETAILED DESCRIPTION

The present invention is an implantable modular orthopedic plate system that includes two or more discrete plate segments that inter-engage. In some embodiments, the discrete segments engage by one or more of engagement features, for example keyed interfitting parts, tongue in groove fittings, and hinges. The implantable modular orthopedic plate system is adapted for sequential deployment of each of the discrete plate segments on bone is adapted to minimize trauma to soft tissue. The implantable modular orthopedic plate system provides an extended length plating system that avoids the need to force a large plate into the smaller soft tissue space. The implantable modular orthopedic plate system is particularly useful in the spine, and more particularly, the cervical spine, where space is extremely limited and the use of plates that are designed to traverse two or more levels presents challenges for placement on the anterior spine while preserving soft tissue integrity.

In use, the implantable modular orthopedic plate system may be provided into the surgical field as a pre-assembled set of at least two plate segments that are hingedly connected in an end to end arrangement and in a fully or partially folded configuration. In other embodiments, the implantable modular orthopedic plate system may be provided into the surgical field as separate plate segments that are individually placed, in sequence, and may be hingedly connected to one another prior to or after placement.

The invention is aimed to diminish or eliminate the risk of esophageal injury because the plate is not forced into the surgical wound. Instead, it is placed in segments in a modular fashion or an accordion fashion and then expanded after it is positioned at the front of the spine below the esophagus and other soft tissues.

The plate system of the invention comprises two or more plate segments that each spans a single level. A single plate segment could be used for one level and multiple plate segments connected together for multiple levels. Thus, two plate segments are connected together for two levels, three plate segments are hinged together for three levels, and so on. The connected plate segments can be folded relative to one another to reduce the length of the system for easier insertion into the space being operated on, especially in multi-level fusion surgery.

When fully deployed, the set of at least two plate segments is sequentially inserted and unfolded into a generally planar configuration along the bone, for example, across adjacent vertebrae, where the plate segments can be fixed in place using suitable bone screws.

The implantable modular orthopedic plate system of the invention includes a set of two or more plate segments (a plurality of plate segments). The plate segments are generally planar and generally square or rectangular in shape, and are adapted to be connected in an end to end configuration. According to embodiments suitable for use in the spine, at least two of the plate segments in the set each spans a single level (i.e., each plate is configured such that its ends can be placed over adjacent vertebrae and the plate spans the disc space therebetween). One or more plates in the set may have at least one engagement end that is one of squared, radiused or lobed at its corners. At least two of the plate segments in the set engage by an overlay of at least a portion of their engagement ends. Thus, each plate includes at one or both ends a surface suitable for overlay engagement with an adjacent plate. The overlaid portions provide reinforcement that resists static and dynamic bending of the plate and provides the advantage of modularity to minimize the overall length of an implant as it is inserted into contact with bone to thereby limit damage to soft tissue.

Each of the plate segments that engage with an adjacent plate segment by a flange may be arranged or folded around a pivot axis and are constrained from rotation by the flange in contact with flange recess on the adjacent connected plate, such that the rotation of each plate segment is limited to up to 90 degrees of rotation away from the contact surface on the back of the flange. In some embodiments, the two connected plate segments are thus movable up to 90 degrees in a manner that draws the lower surfaces of the plate segments toward one another. In some other embodiments, the flange and flange seat may be oriented such that the two connected plate segments are thus movable up to 90 degrees in a manner that draws the upper surfaces of the plate segments toward one another.

In some embodiments, at least two of each of the two or more plate segments inter-engage by at least overlay interfitting of flange and flange recess features, and may also be hingedly connectible. According to such embodiments, two or more plate segments may be connectible by hinged engagement. Hinged engagement of plate segments may be achieved by fixed hinges and releasable hinges. In some embodiments, the fixed hinges comprise one or a plurality of receiving channels on the engagement ends of the plate segments and an engagement pin for fixing them together. In other embodiments, the releasable hinges comprise one or a plurality of engagable arcuate flanges on the engagement ends of adjacent plate segments. In yet other embodiments the plate segments may be joined by other join or alignment means as described herein and as known in the art. In the various embodiments, each of the flange and the flange recess that are in contact between adjacent plates includes at least one securement hole, wherein the flange and flange recess securement holes are aligned when the flange is contacted with the flange recess.

In some embodiments, the set includes additional plate segments that join adjacent plate segments, and such plate segments may or may not overlap all or partially with an adjacent plate.

The plate segments have width, length and depth/thickness dimensions that are consistent with those generally known in the orthopedic plate art. In various embodiments, plate segments may have a thickness in the range from about 1-10 mm in thickness, 10-60 mm in width, and 10-100 mm in length. In some embodiments, especially for use in the cervical spine, each plate has one or more of a thickness dimension in the range from about 2 to about 3 mm, a width dimension in the range from about 6 to about 10 mm, and a length dimension in the range from about 20 to about 30 mm.

Implantable Modular Orthopedic Plate Systems

Referring now to the drawings, FIG. 1 shows a first embodiment of an implantable modular orthopedic plate system. Each of FIG. 1-FIG. 9 show alternate views of a hinged plate system 100 according to the disclosure. As shown, the representative example of the hinged plate system 100 includes two plate segments, including a base plate 110 and an extension plate 120. It will be appreciated that this system is adapted for fixation to adjacent vertebrae in a spine, for example, a human spine, and is a two-level plate, which means that the hinged plate system 100 traverse two levels (i.e., two disc spaces) and includes securement holes 200 suitable for passage of a fixation element, such as a screw, through the securement holes 200 and into each of three vertebrae. In the various embodiments, each plate segment includes at least one securement hole 200. In some embodiments, a plate segment includes two securement holes 200. In some embodiments, a plate segment includes more than two securement holes 200. And in some embodiments, a plate segment includes four securement holes. As depicted in the drawings, securement holes 200 in the plates are oriented in the region of an outer corner of a plate segment, and most plate segments include securement holes on each of the two corners of at least one end of a plate segment. Of course, more securement holes 200 may be employed, and fewer securement holes may be employed. For example, a plate segment may have three or four securement holes 200 along an edge of the plate segment, such as an engagement end. Or a plate segment may have a single securement hole 200 oriented along an edge of the plate segment, such as an engagement end. In the various embodiments, each of a plate having flange recess adapted for receiving either a flange or an insert 820 and a plate having flange adapted for contacting a flange recess will include at least one securement hole 200 for passage of a screw or other securement means therethrough to secure the plate segments together to bone.

One or more plates in an implantable modular orthopedic plate system includes an access aperture 300, which provides one or both of visualization of a disc space or access to the space for inserting bone morphogenic and graft materials. As mentioned herein above, the various embodiments of the implantable modular orthopedic plate system are particularly suited for use in the cervical spine, though it will be appreciated that an implantable modular orthopedic plate system according to the disclosure is suitable for use along any segment of a spine, and cold be adapted for use in the context of other bones. As depicted, this particular hinged plate system 100 is a terminal system, in that it is not configured to be extended at either of its opposite ends 111, 122. Of course, in other examples, the extension plate 120 could be replaced with alternate plate segments as further described herein which are non-terminal extension plate segments.

Figure 2:
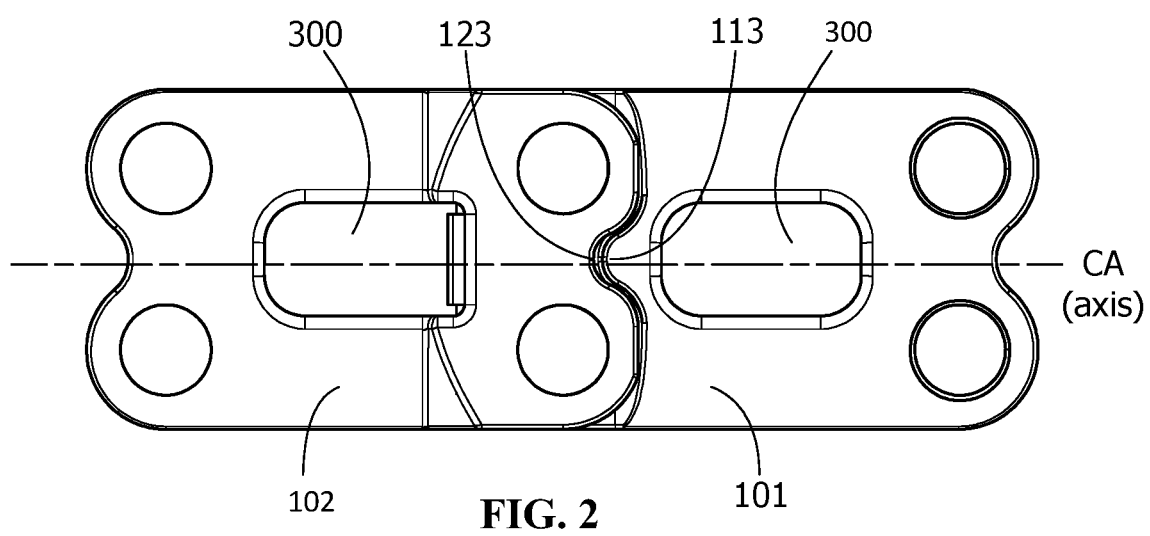
FIG. 2 is a top view of the implantable modular orthopedic plate system shown in FIG. 1.
Figure 3:
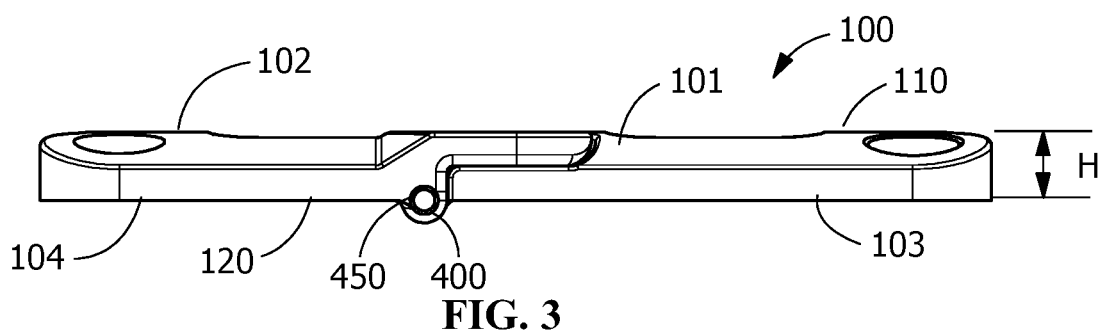
FIG. 3 is a side view of the implantable modular orthopedic plate system shown in FIG. 1.
Figure 4:
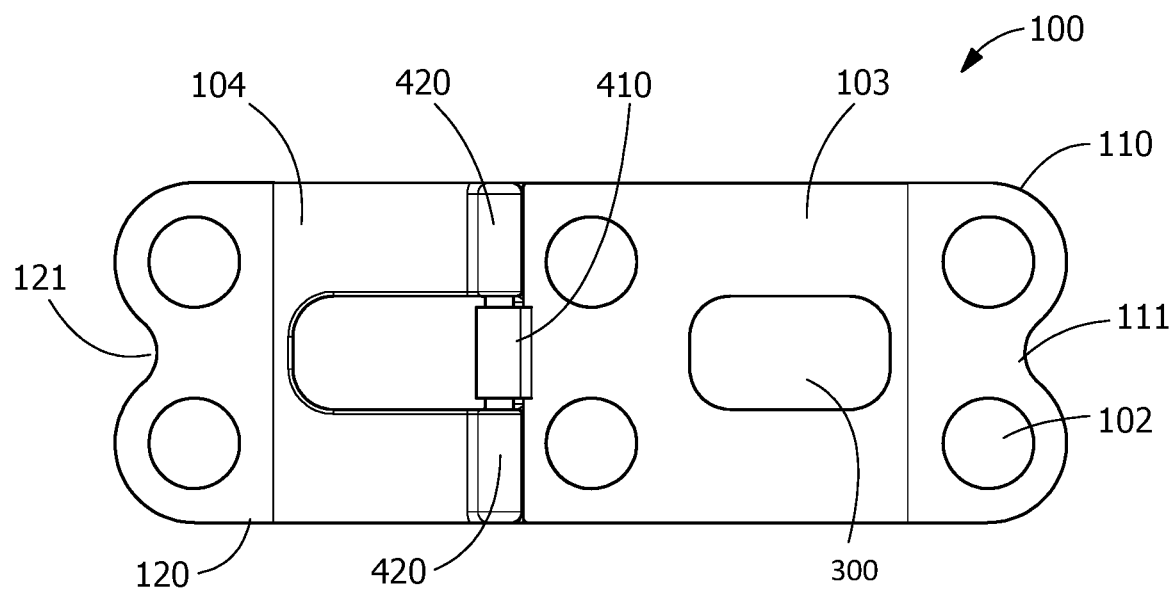
FIG. 4 is a bottom view of the implantable modular orthopedic plate system shown in FIG. 1.
Figure 5:
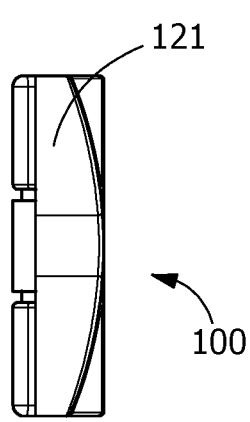
FIG. 5 is a first end view of the implantable modular orthopedic plate system shown in FIG. 1.
Figure 6:
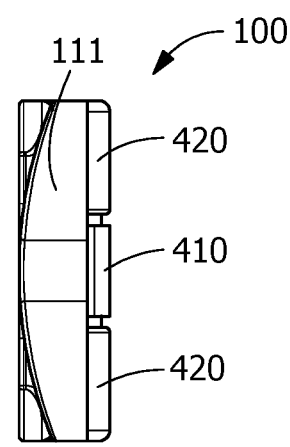
FIG. 6 is a second end view of the implantable modular orthopedic plate system shown in FIG. 1.

Referring now to FIG. 1 and FIG. 4, each of the base plate 110 and the extension plate 120 has an upper surface (base) 101 and an upper surface (extension) 102, and each has a lower surface (base) 103 and a lower surface (extension) 104. Likewise, with reference to FIG. 1, FIG. 4 and FIG. 5-FIG. 6, the base plate 110 has a free end (base) 111 and an engagement end (base) 112 and the extension plate 120 has a free end (extension) 121 and engagement end (extension) 122. As shown in FIG. 1 and FIG. 2, each of the base plate 110 and the extension plate 120 include an engagement feature in the form of shaped/keyed engagement, the base plate including on its upper surface 101 a male key 113 that engages with a corresponding female key 123 at the engagement end 122 of the extension plate 120.

Figure 7:
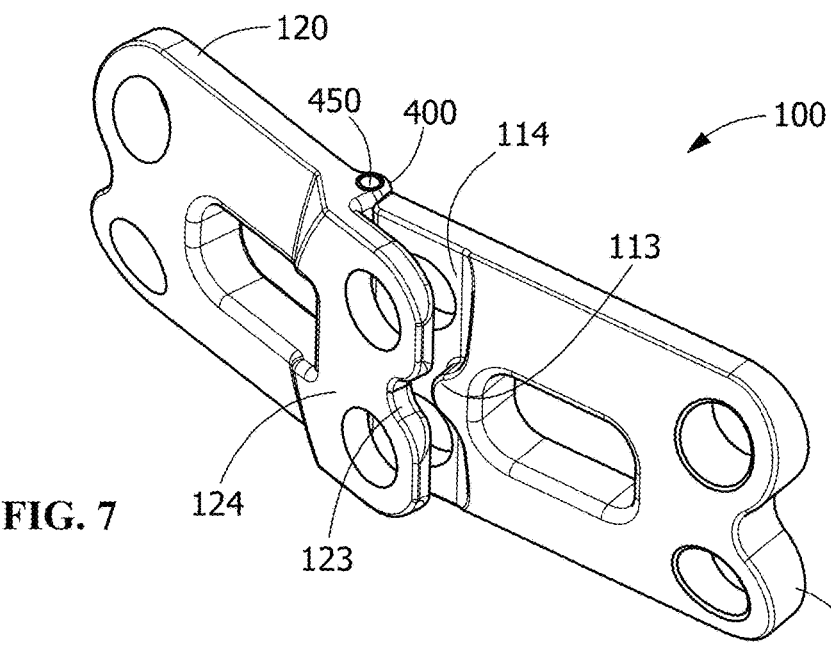
FIG. 7 is an alternate front perspective view of the implantable modular orthopedic plate system shown in FIG. 1.
Figure 8:
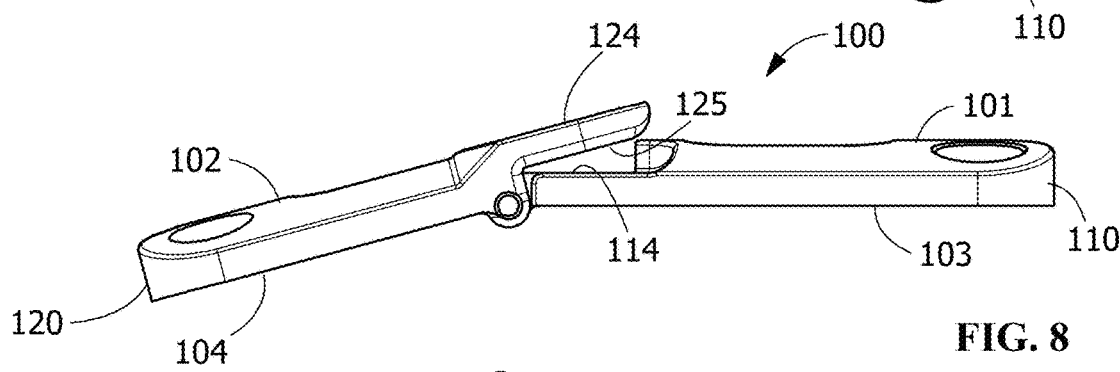
FIG. 8 is an alternate side view of the implantable modular orthopedic plate system shown in FIG. 1.
Figure 9:
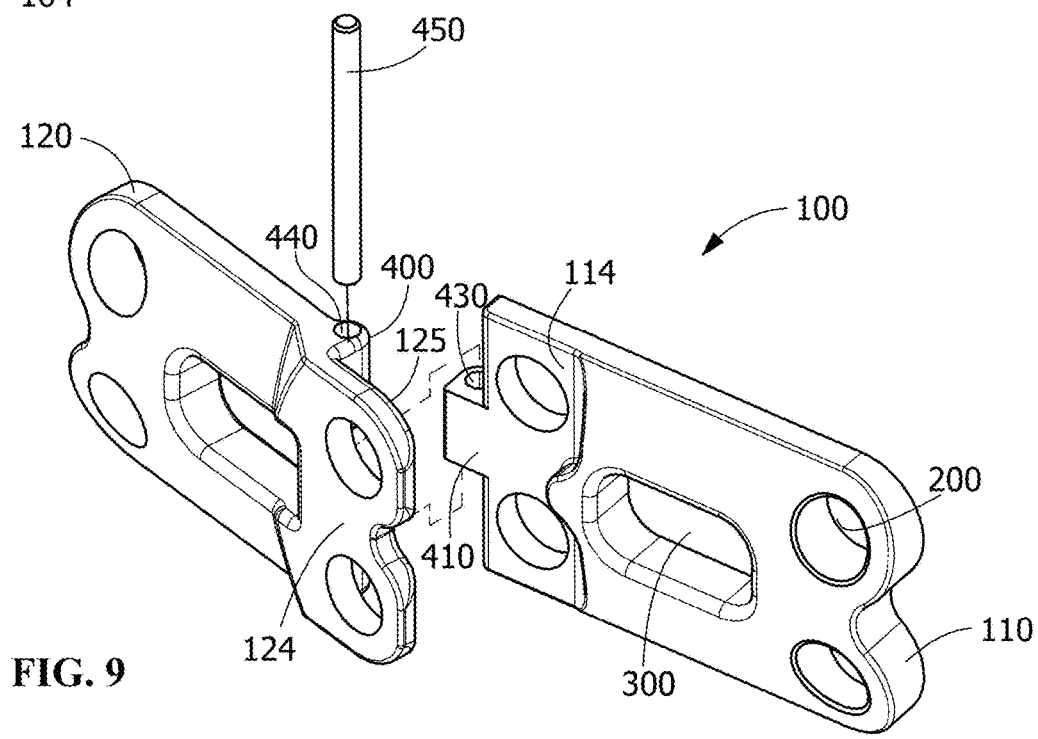
FIG. 9 is an exploded front perspective view of the implantable modular orthopedic plate system shown in FIG. 1.

Referring now to FIG. 7, the base plate 110 includes a flange recess 114 that forms a set for receiving a flange 124 on the engagement end 122 of the extension plate 120. The flange recess 114 is complementary to the flange back 125 and the two surfaces are contacted when the hinged plate system 100 is assembled to provide a secured and reinforced interface between the two plate segments. As shown the engagement ends 112 and 122 include corresponding securement holes 200 which are aligned with the flange recess 114 and flange back 125 are contacted, and can thus receive a fixation element, such as a screw, through the aligned securement holes 200 to lock the plate segments together to be secured to bone.

It will be appreciated that in the various embodiments herein, the engagement between corresponding plate segments that include the flange recess and flange engagement, such plate system assemblies will not permit full pivotal motion between the engaged plates, if any. Thus, the embodiments herein that allow for pivotal movement between engaged plates that include the feature of flange recess and flange engagement will permit pivotal movement of one or both plate segments only away from the flange back surface insofar as the flange restricts any rotation of the plates out of plane in the other direction. According to the various embodiments, the term flange herein refers to a structure that is raised or cantilevered from the plane of a plate segment such that the upper surface of the flange is not in the same plane as the upper surface of the non-flange portion of the plate segment.

With references to the drawings herein of the different embodiments of the implantable modular orthopedic plate system as shown variously in the drawings, for example in FIG. 1-FIG. 9, the plate segments are shown as having generally planar lower surfaces 103, 104, and contoured upper surfaces 101, 102 that are slightly domed at their centers along a centerline axis (CA) of the plate assembly. Further, the plate segments as shown variously in the drawings, for example in FIG. 1-FIG. 9, include contoured ends 111, 112, 121, 122 with radiused lobe shapes. Further, the plate segments as shown variously in the drawings, for example in FIG. 1-FIG. 9, include at their engagement ends 112, 122 the complementary flange back 125 and flange recess 114 which are generally planar.

It will be appreciated that in alternate embodiments, the plate segments of the implantable modular orthopedic plate system as shown variously in the drawings, for example in FIG. 1-FIG. 9 may have lower surfaces that are other than planar. For example, the lower surfaces of any one or more plate segments may have a contour that is suitable for more closely matching the surface of bone which will be contacted by the lower surfaces when affixed to bone. Or the lower surfaces may be textured, ribbed, knurled or have other surface features that enable frictional securement from sliding on the bone surface. Likewise, the upper surfaces of any one or more plate segments may a different contour that is not arced or domed, and may, for example, be planar.

It will also be appreciated that any one of the ends of the plate segments according to the various embodiments may have one or more ends that do not include lobed contouring. For example, any plate segment according to the disclosure may have an end that is squared, or radiused or a combination thereof, and may be chamfered, or beveled or may include other features such as one or more flanges, or grooves. Further, while the contact surfaces that include the flange recess 114 and the flange back 125 may be planar, as shown in the various drawings, it will be appreciated that these complementary surfaces may have any other shape or texture or combination thereof that is suitable for complementary engagement when the surfaces are contacted.

Referring now to FIG. 1 and FIG. 7, the hinged plate system 100 includes a hinge 400 that comprises a pin 450 that is slidably engaged in receivers 430, 440 in each of the plate segments 110, 120. The receivers are formed in interdigitating extensions at the engagement ends 112, 122 of the two plate segments which interdigitating extensions, when aligned, provide a continuous receiver channel for the pin 450. Referring now to FIG. 4, the base plate 110 includes a center digit 410 and the extension plate 120 includes a pair of outer digits 420, the center digit including a center digit receiver 430 and the outer digits 420 including an outer digit receiver 440. It will be appreciated that different configurations are possible for the interdigitating digits and the receiver channel formed thereby. For example, a pair of outer digits may be on the base plate segment 110 and the single center digit may be on the extension plate segment 120. Further, the two plate segments may have more or fewer digits where in one example of fewer digits, each plate segment may have a single laterally oriented digit at opposite side edges of the two plate segments. Further still, while the receivers 430, 440 are shown as having solid, generally cylindrical inner walls, in other embodiments, the receivers may include a slot or hemi shape for example a hemi cylindrical shape and each plate segment may have one or more digits with hemi shapes, such as hemi cylindrical, that are oriented with the slots aligned or not aligned.

It should be appreciated as noted above that while the embodiment of the implantable modular orthopedic plate system shown in FIG. 1-FIG. 9 includes terminal plate segments, other embodiments as of plate segments described herein are non-terminal and include features that one or more plates in an assembly to receive an additional plate. Such embodiments allow for sequential placement of additional plates along bone, in one or both directions relative to a plate, which placement may be accomplished in a single surgical procedure, or may be accomplished in a later procedure when additional levels of fixation and/or fusion are required.

In other embodiments according to the disclosure, an implantable modular orthopedic plate system may include terminal or non-terminal plate segments that can be engaged with one another in a loose orientation whereby they are contacted and aligned by cooperation of contact features, such as, but not limited to the keyed features as described above in relation to the embodiment of FIG. 1-FIG. 9, wherein it will be appreciated that such keyed features may have a variety of interfitting shapes, such as the male/female radiused contours. For example, the shaped or keyed interfitting features may be generally squared, or wavy, or combinations thereof, the features serving the function of loosely aligning the plate segments prior to locking them together by passage of a fixation element, such as a screw or bone plug or the like.

In some embodiments as further shown in FIG. 10-18, the plate segments may be engaged by interaction of complementary engagement features that one or more of slide, snap or interdigitate. In some embodiments, the engagement features are releasable, enabling assembly of the plate system in the surgical site in a serial manner. Or two or more segments may be assembled prior to placement in the surgical site. In some embodiments, the engagement features include tongue in groove structures that allow engagement of the plate segments across their lateral dimension transverse to the center line axis of the assembled plate system. Some such embodiments enable hinged movement of the plate segments, and other embodiments restrict the plate segments to a single plane once connected.

It will be appreciated that in various possible embodiments according to the disclosure, any of the single plates may be employed without another plate wherein a signal plate is useful in a spinal application for only a single level.

In some embodiments, a system including two plates may be either terminal (i.e., adapted for engagement with another plate segment only at one end), or non-terminal and extendible in one or both directions. Further, any of the plate engagement features herein may be combined when employing a system that includes more than two plate segments. Thus, in some embodiments, all plate segments may be joined by the same engagement means, such as hinges, opposing arcuate flanges, in line tongue in groove, loose alignment, snap fit, and combinations thereof. In other embodiments, adjacent plate segments may be joined by a combination of engagement means, selected from hinges, opposing arcuate flanges, in line tongue in groove, loose alignment, snap fit, and combinations thereof. Further, in multi-plate systems, as shown, for example, in FIG. 19, some adjacent plate segments may be engaged for pivotal motion in one direction relative to the plane of the assembly, and others in another direction, and some plates may include flanges and others will not include flanges.

Referring again to FIG. 9, the plate on the left includes at its engagement end and below the flange a receiving channel for a pin and the plate on the right includes at its engagement end and extending from the overlay seat a pin receiving channel that interfits with the pin receiving channel on the adjacent plate which when engaged touger the plate segments receive a pin that enables pivotal motion around the pin away from the overlay and toward the bottom of the plate. As shown in the drawings, systems that include more than two plate segments are arranged for alternate rotation of adjacent plate around their pivot axes in order to achieve full or partial folding of the implantable modular orthopedic plate system, as demonstrated in FIG. 19-32.

Figure 10:
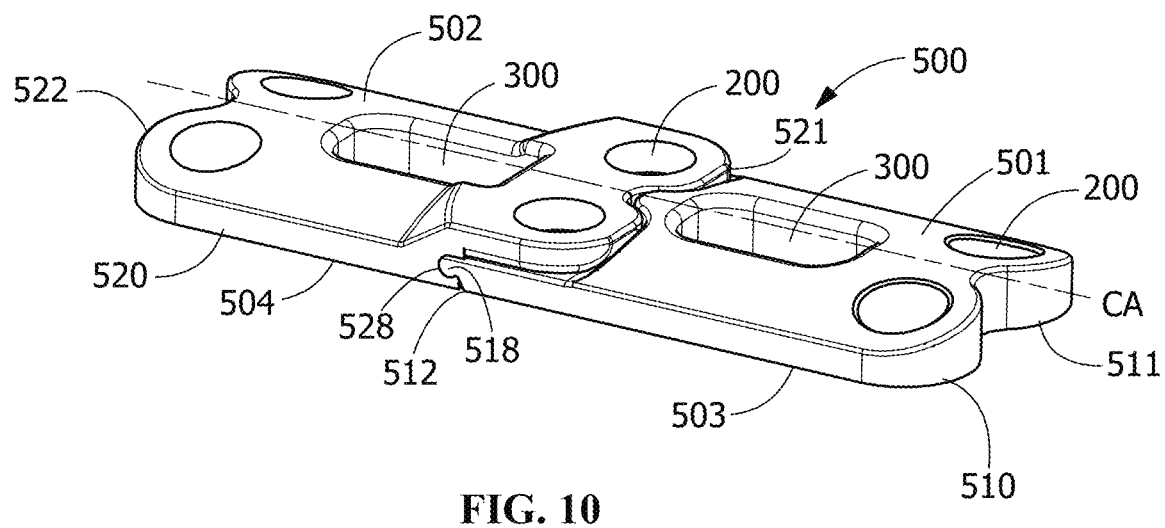
FIG. 10 is a front edge perspective view of an alternate embodiment of an implantable modular orthopedic plate system according to the disclosure.
Figure 11:
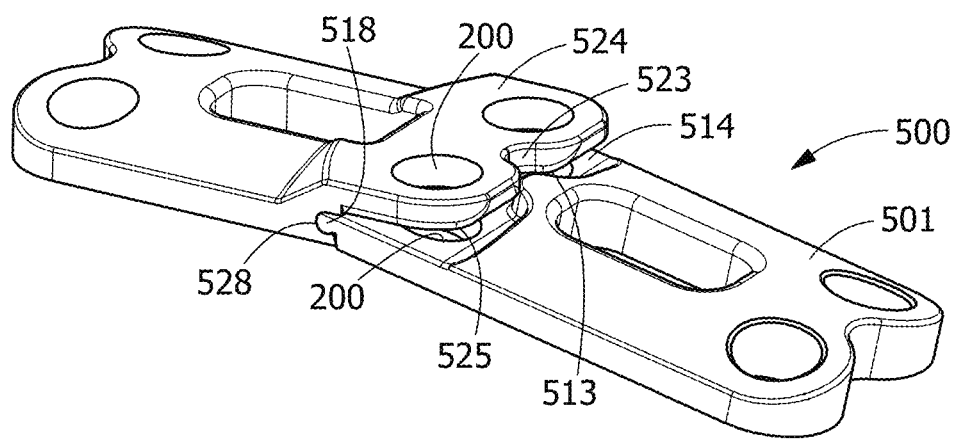
FIG. 11 is an alternate view of the embodiment of the implantable modular orthopedic plate system shown in FIG. 10.

Referring now FIG. 10, another embodiment of an implantable modular orthopedic plate system is shown. Each of FIG. 10-FIG. 11 shows alternate views of an in-line engagement plate system 500 wherein the plate segments may be fixedly or releasably engaged.

With reference to the drawings, it will be appreciated that the plate segments of the in-line engagement plate system 500 include several analogous structural features with those described above with respect to the embodiment of the implantable modular orthopedic plate system shown in FIG. 1-FIG. 9. And like the embodiment of the implantable modular orthopedic plate system in FIG. 1-FIG. 9, some of these features may be varied as described above. Referring now to FIG. 10, the in-line engagement plate system 500 includes a base plate 510 and an extension plate 520. The base plate 510 and the extension plate 520 each respectively includes an upper surface (base) 501 and upper surface (extension) 502, and a lower surface (base) 503 and a lower surface (extension) 504. Further the base plate 510 includes a free end (base) 511, an engagement end (base) 512, a male key 513, a flange recess 514, and the extension plate 520 includes a free end (extension) 522, an engagement end (extension) 521, a female key 523, a flange 524, and a flange back 525.

Referring again to the FIG. 10, the in-line engagement plate system 500 includes a tongue-in-groove engagement that is in line with the respective engagement ends 512, 521 of the plate segments 510, 520. The tongue-in-groove engagement includes a tongue 518 and a groove 528 that inter-engage along the width dimension of each of the plate segments, wherein the engagement is in line such that the ends of the plate segments abut at the lower surfaces 503, 504. As shown in the depicted embodiment, the tongue 518 is on the base plate segment 510 and the groove 528 is on the extension plate segment 520, but it will be appreciated that the position of each of the features may be switched. Further, while in the depicted embodiment each of the tongue 518 and the groove 528 extends across the entire width of the respective plate segments 510, 520, in other embodiments, the complementary features may be present only in the middle of the plate segments, or at the lateral edges of the plate segments, or may be a combination of these such that the features are not continuous across the width dimension of the plate segments. Further, the tongue-and-groove features may be snap fit or may be slidably engaged along the shared pivot axis PA. In some embodiments, the engagement allows pivotal movement between the plates and in other embodiments that plates are fixed in a single plane when engaged.

Figure 12:
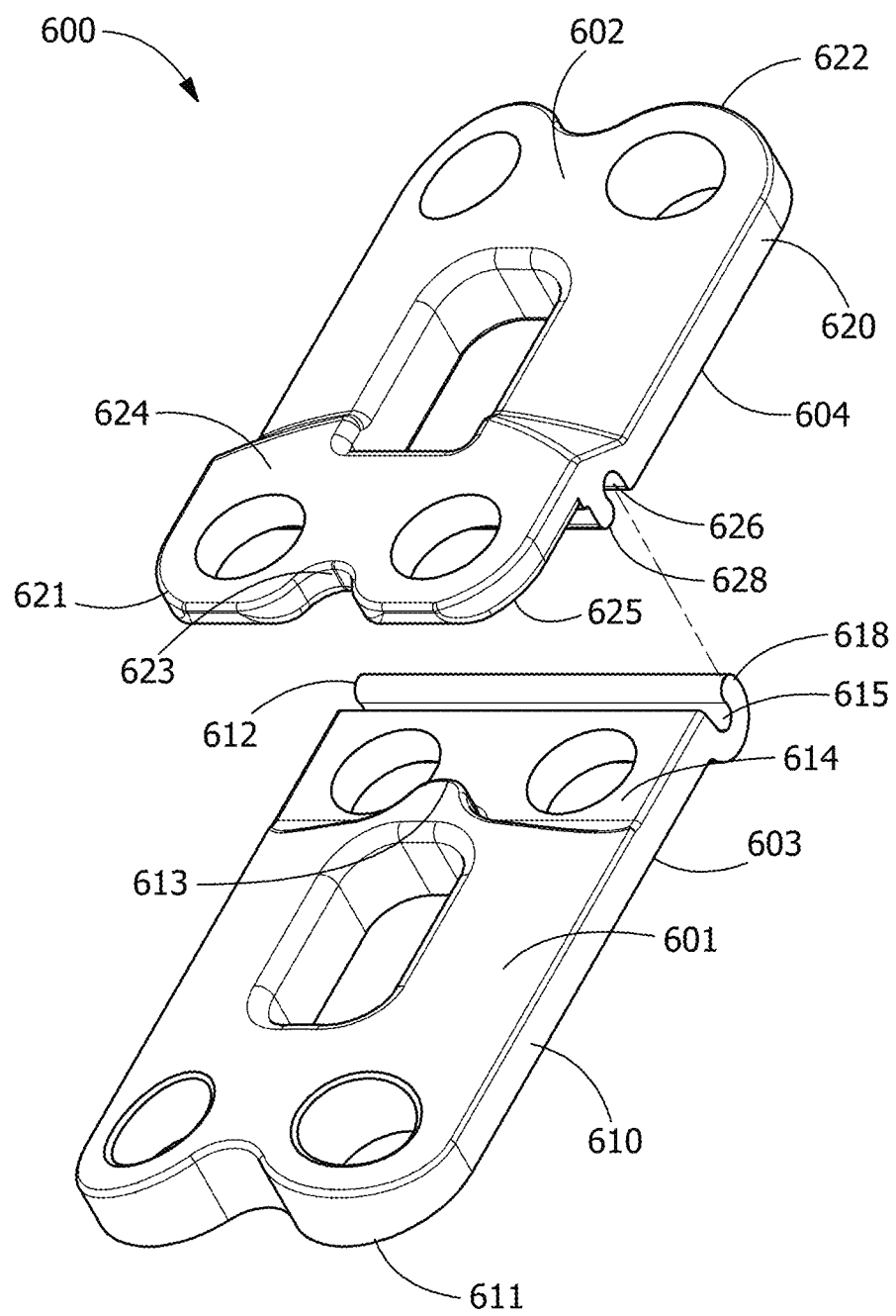
FIG. 12 is an exploded front perspective view of an alternate embodiment of an implantable modular orthopedic plate system according to the disclosure.
Figure 13:
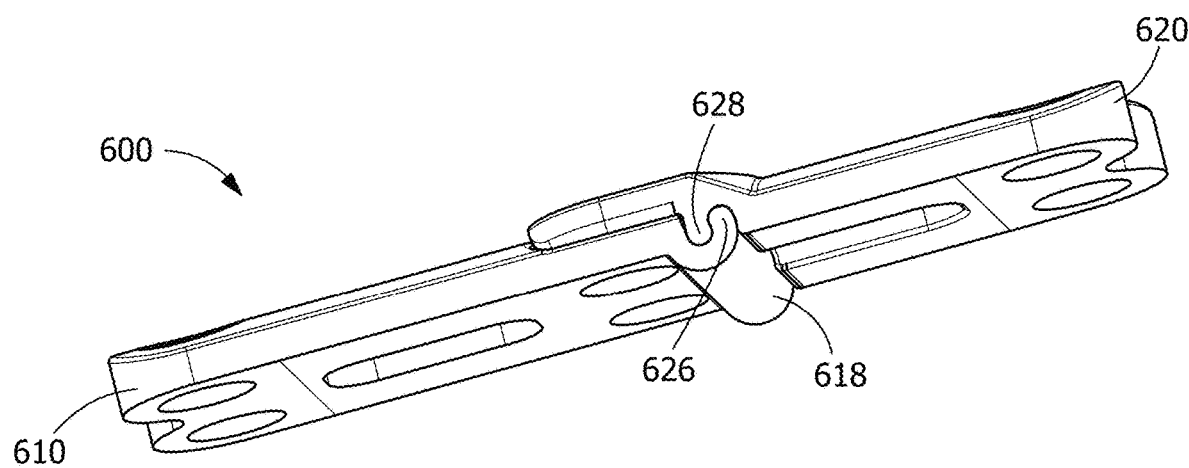
FIG. 13 is a bottom edge perspective view of an alternate embodiment of an implantable modular orthopedic plate system according to the disclosure.
Figure 14:
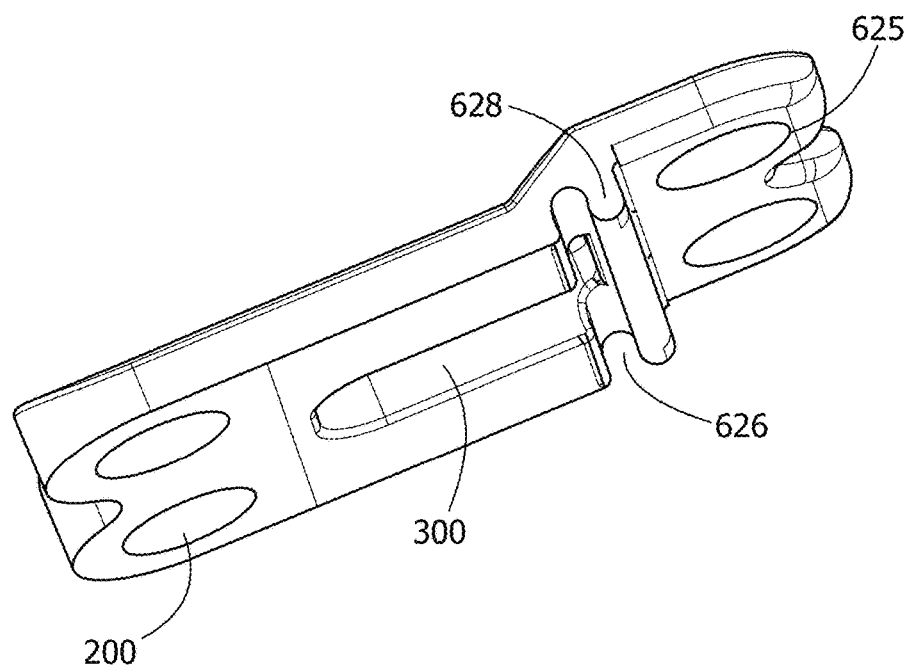
FIG. 14 is a bottom edge perspective view of a plate component of the implantable modular orthopedic plate system shown in FIG. 13.

Referring now FIG. 12, another embodiment of an implantable modular orthopedic plate system is shown. Each of FIG. 12-FIG. 14 show alternate views of an undercut releasable engagement plate system 600 according to the disclosure.

With reference to the drawings, it will be appreciated that the plate segments of the undercut releasable engagement plate system 600 include several analogous structural features with those described above with respect to the embodiment of the implantable modular orthopedic plate system shown in FIG. 1-FIG. 9. And like the embodiment of the implantable modular orthopedic plate system in FIG. 1-FIG. 9, some of these features may be varied as described above. Referring now to FIG. 12, the undercut releasable engagement plate system 600 includes a base plate 610 and an extension plate 620. The base plate 610 and the extension plate 620 each respectively includes an upper surface (base) 601 and upper surface (extension) 602, and a lower surface (base) 603 and a lower surface (extension) 604. Further the base plate 610 includes a free end (base) 611, an engagement end (base) 612, a male key 613, a flange recess 614, and the extension plate 620 includes a free end (extension) 622, an engagement end (extension) 621, a female key 623, a flange 624, and a flange back 625.

The base plate and extension plate segments 610, 620 as shown in FIG. 12 are connected together with a releasable hinge structure that comprises on the engagement end of each of the plate segments 610, 620 an arcuate flange that includes a groove and a corresponding tongue to form a tongue-in-groove engagement, the flanges adapted for engagement to form a pivot axis.

Referring again to FIG. 12, the tongue-in-groove engagement includes an arcuate engagement feature on the engagement end 612 of the base plate segment 610, the engagement feature including a retainer tongue 618 and a retainer groove 615 that inter-engages along the width dimension of the base plate segment 610 with a corresponding engagement feature on the engagement end 621 of the extension plate segment 620. The extension plate segment 620 includes an undercut that forms an extension tongue 628 and an extension groove 626, wherein the extension tongue 628 engages within the retainer groove 615 and the extension groove 626 receives the retainer tongue 618 of the base plate 610. According to this embodiment, the engagement of the plate segments 610, 620 includes the insertion of the arcuate flange into contact with the undercut tongue and groove. As shown in the depicted embodiment, the retainer tongue 618 and retainer groove 615 are on the base plate segment 610 and the extension tongue 628 and extension groove 626 are on the extension plate segment 620, but it will be appreciated that the position of each of the features may be switched. Further, while in the depicted embodiment each of the tongue and the groove features extends across the entire width of the respective plate segments 610, 620, in other embodiments, the complementary features may be present only in the middle of the plate segments, or at the lateral edges of the plate segments, or may be a combination of these such that the features are not continuous across the width dimension of the plate segments. Further, the tongue-and-groove features may be snap fit or may be slidably engaged along the shared pivot axis PA. In some embodiments, the engagement allows pivotal movement between the plate segments wherein the pivotal motion is restricted by interaction between the flange and flange recess, and in other embodiments the plate segments are fixed in a single plane when engaged.

Figure 15:
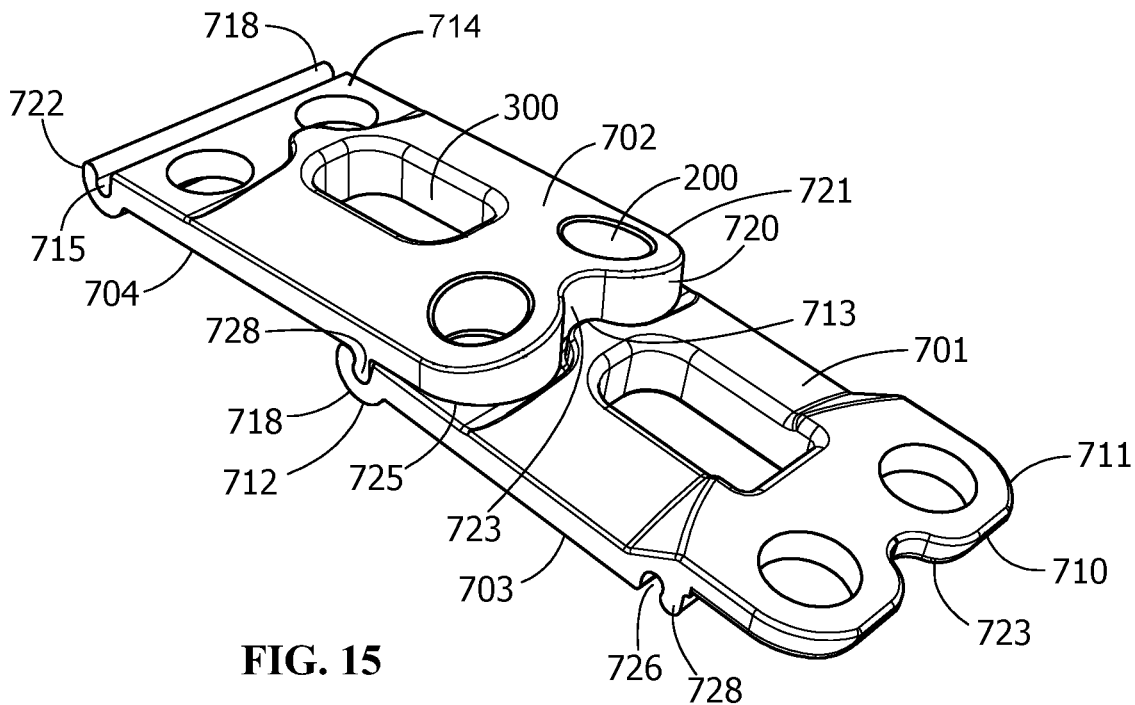
FIG. 15 is a front perspective view of an alternate embodiment of an implantable modular orthopedic plate system according to the disclosure.

Referring now FIG. 15, another embodiment of an implantable modular orthopedic plate system is shown. The depicted embodiment is a non-terminal extendible system that allows for extension at each of the ends of the assembled plate system. As shown the extendible engagement plate system 700 includes tongue and groove engagement features.

With reference again to FIG. 15, it will be appreciated that the plate segments of the extendible engagement plate system 700 include several analogous structural features with those described above with respect to the embodiment of the implantable modular orthopedic plate system shown in FIG. 1-FIG. 9. And like the embodiment of the implantable modular orthopedic plate system in FIG. 1-FIG. 9, some of these features may be varied as described above. Referring again to FIG. 15, the extendible engagement plate system 700 includes a base plate segment 710 and an extension plate segment 720. The base plate 710 and the extension plate 720 each respectively includes an upper surface (base) 701 and upper surface (extension) 702, and a lower surface (base) 703 and a lower surface (extension) 704. Further the base plate segment 710 includes a free end (base) 711, an engagement end (base) 712, a male key 713, a contact recess 714, and the extension plate segment 720 includes a free end (extension) 722, an engagement end (extension) 721, a female key 723, and a contact back surface 725.

As shown, the depicted embodiment of the base plate 710 includes an extension groove 726 and an extension tongue 728, and the extension plate segment 720 includes a retainer groove 715 and a retainer tongue 718. The extension plate segment 720 is adapted to receive another plate segment via engagement with its arcuate feature that comprises the retainer groove 715 and a retainer tongue 718, such plate segment may be selected from another extension plate segment 720 or another base plate segment 710. The extension plate segment 720 also includes a recess 714 at its free end 722 adjacent to the retainer groove 715 and retainer tongue 718, the recess suitable for receiving one of a flange from another plate segment, or an insert 820, as shown in FIG. 16, the insert suitable for providing supplemental strength to the plate if secured to bone without an extension plate.

Figure 18:
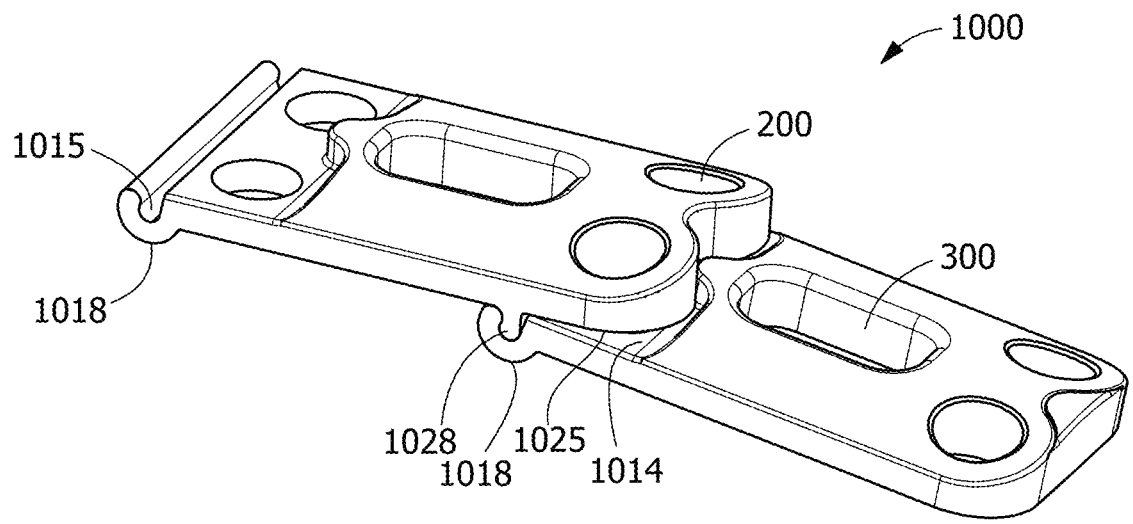
FIG. 18 is a front perspective view of an alternate embodiment of an implantable modular orthopedic plate system according to the disclosure.

Likewise, the base plate segment 710 is adapted to receive another plate segment via engagement with the undercut that forms its extension tongue 728 and extension groove 726, such plate may be selected from another extension plate segment 720 or another base plate segment 710. Referring now to FIG. 18, the drawing depicts a plate system 1000 that includes two plate segments that correspond with the extension plate segment 720 shown in FIG. 15, the plates engaged in a tongue-in-groove engagement that is not in-line. The plate system 1000 includes on the base plate 1010 a flange recess 1014 and a retainer tongue 1018, and includes on the extension plate 1020 a back 1025, a tongue 1028 for engagement with the groove 1015 of the retainer tongue 1018 on the engagement end of the base plate 1010, and at its free end a further tongue in groove feature that includes a groove 1015 and a retainer tongue 1018.

Figure 16:
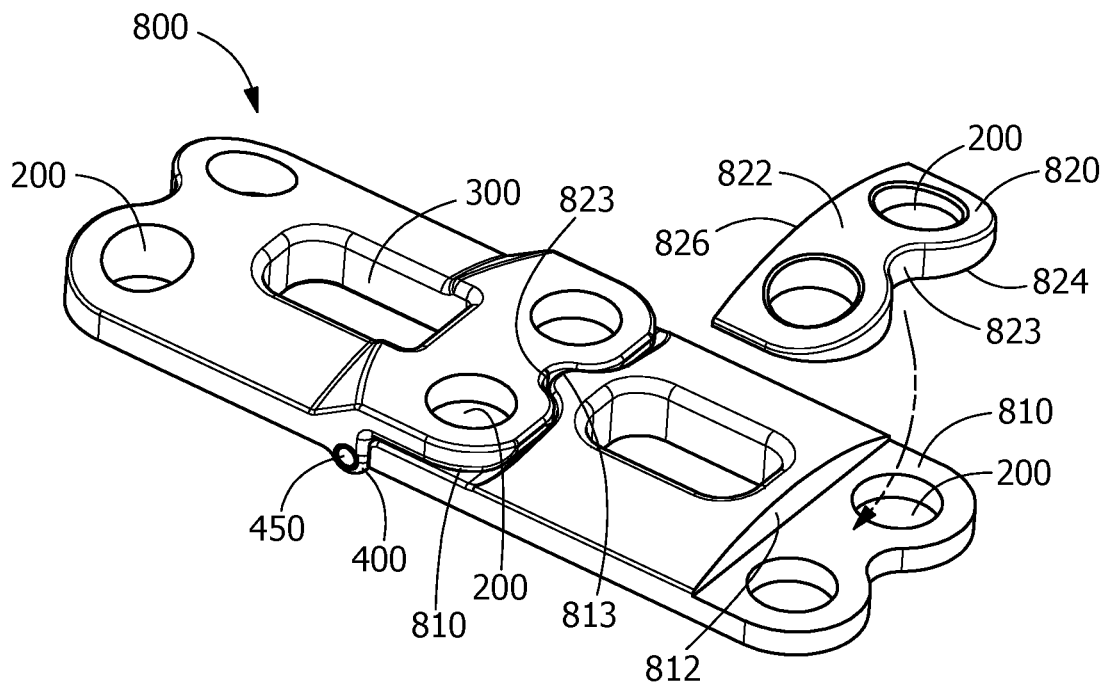
FIG. 16 is a front perspective view of an alternate embodiment of an implantable modular orthopedic plate system according to the disclosure.
Figure 17:
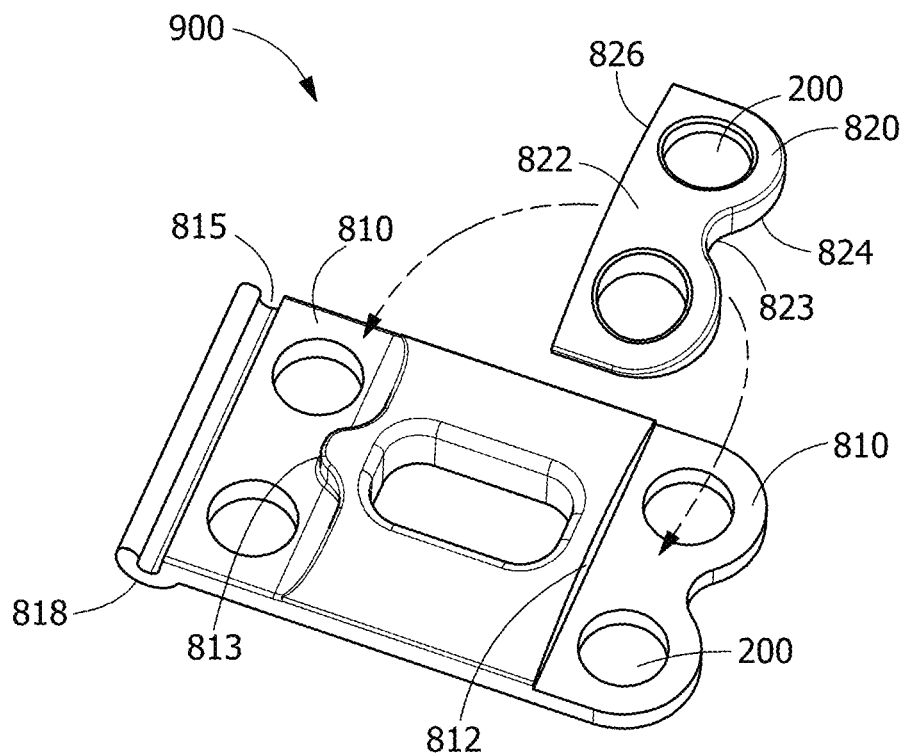
FIG. 17 is a front perspective view of a plate segment of an alternate embodiment of an implantable modular orthopedic plate system according to the disclosure.

Referring now to FIG. 16 and FIG. 17, it will be appreciated that the plate segments shown include several analogous structural features with those described above with respect to the embodiment of the implantable modular orthopedic plate system shown in FIG. 1-FIG. 9. And like the embodiment of the implantable modular orthopedic plate system in FIG. 1-FIG. 9, some of these features may be varied as described above. With reference again to FIG. 16, another embodiment of an implantable modular orthopedic plate system is shown as a variation on the embodiment shown in FIG. 1, except the free end of the base plate includes a flange recess 810 that is adapted to receive a flange from an extension plate or an insert 820 that is suitable for providing supplemental strength to the plate if secured to bone without an extension plate. The flange recess 810 is adapted to contact a lower face 824 of the insert 820, and includes an insert abutment 812 for interfacing with an insert edge 826 on the insert 820. The insert 820 is provided with a free end 821 that is contoured to correspond with the contoured free end of the base plate 810, and likewise is contoured to key with a male key 813. FIG. 17 shows a variation of the extension plate segment 720 in FIG. 15. The double extension plate segment 900 includes two flange recesses 810, each adapted to engage with either a flange or an insert 820. The insert 820 includes an insert edge 826, a lower surface 824, and upper surface 822, and a female key 823.

Figure 19:
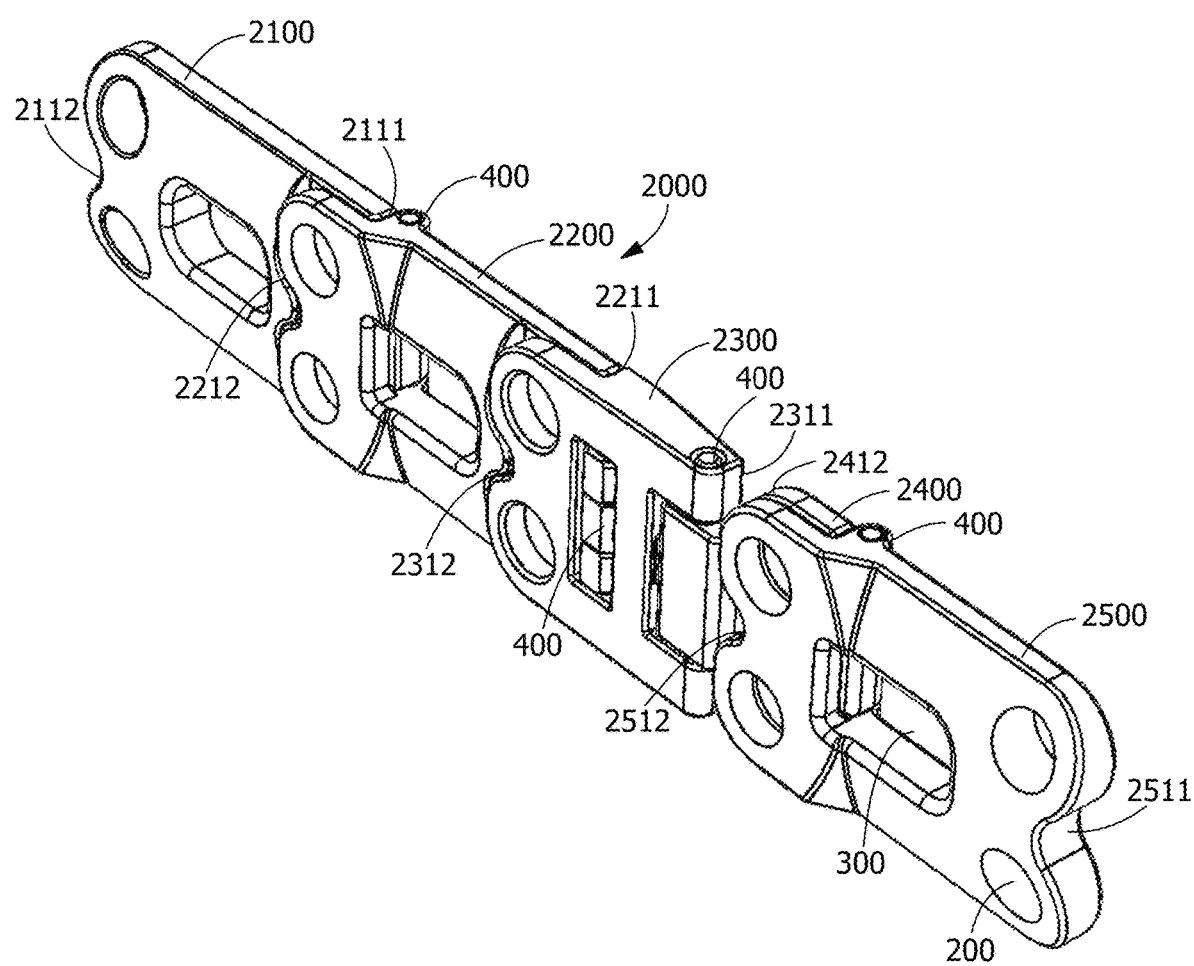
FIG. 19 is a front perspective view of an alternate embodiment of an implantable modular orthopedic plate system according to the disclosure.
Figure 20:
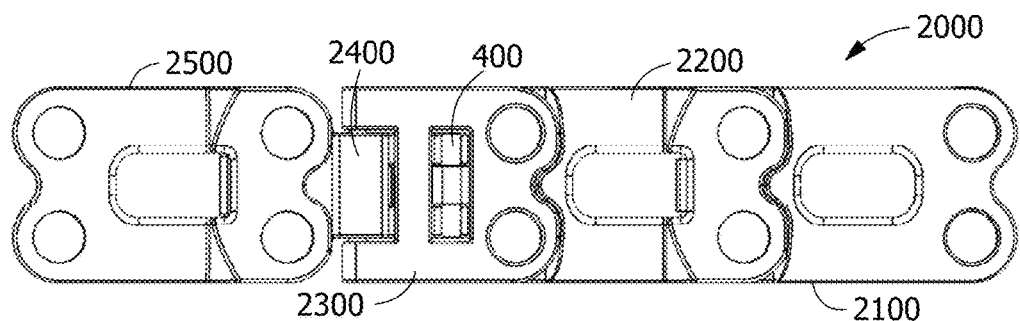
FIG. 20 is a top view of the implantable modular orthopedic plate system shown in FIG. 19.
Figure 21:
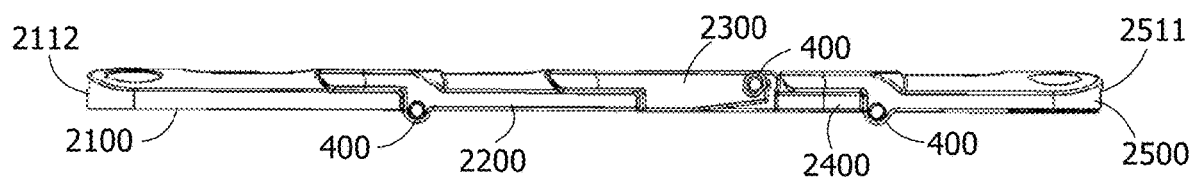
FIG. 21 is a side view of the implantable modular orthopedic plate system shown in FIG. 19.
Figure 22:
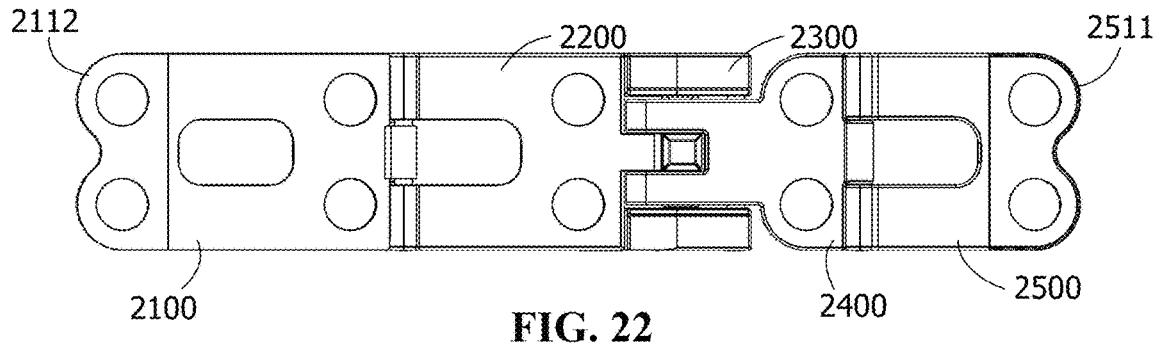
FIG. 22 is a bottom view of the implantable modular orthopedic plate system shown in FIG. 19.
Figure 23:
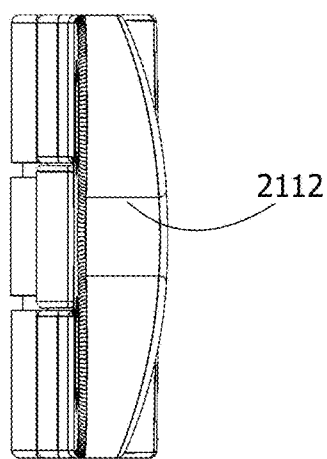
FIG. 23 is a first end view of the implantable modular orthopedic plate system shown in FIG. 19.
Figure 24:
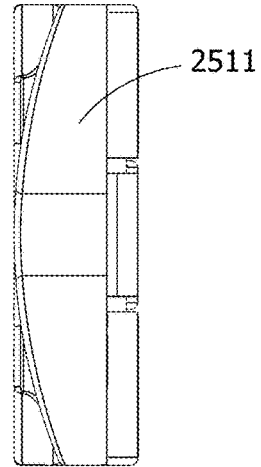
FIG. 24 is a second end view of the implantable modular orthopedic plate system shown in FIG. 19.
Figure 25:
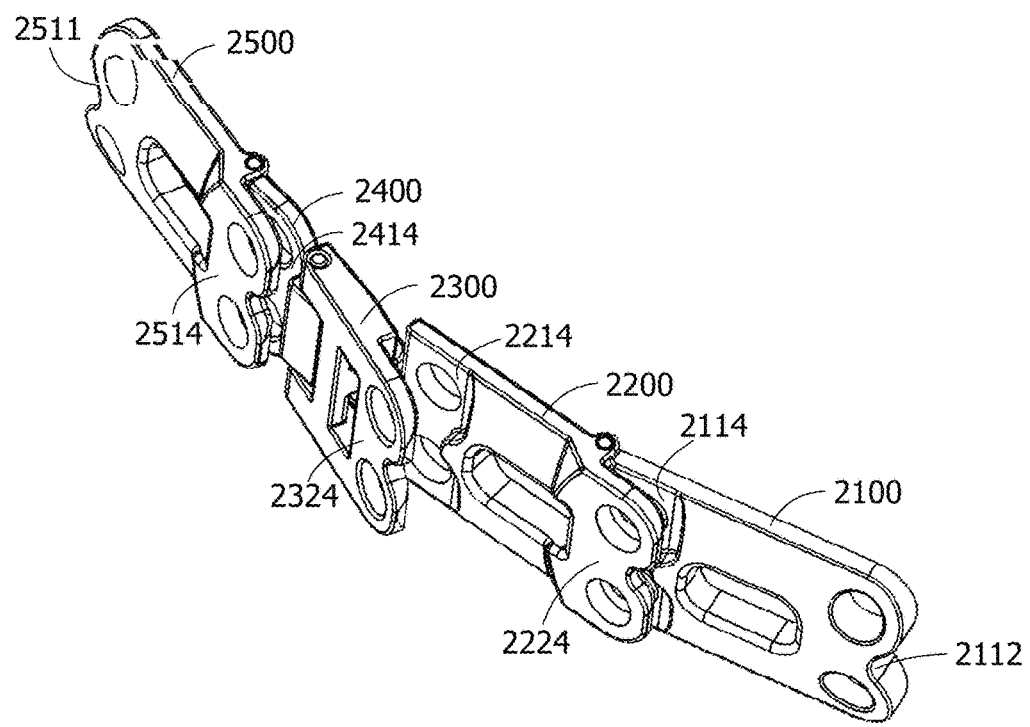
FIG. 25 is an alternate perspective view of the implantable modular orthopedic plate system shown in FIG. 19.
Figure 26:
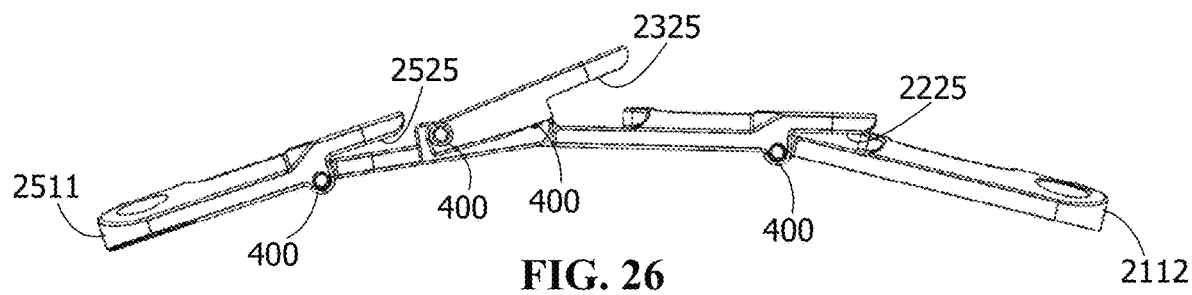
FIG. 26 is an alternate side view of the implantable modular orthopedic plate system shown in FIG. 19.
Figure 27:
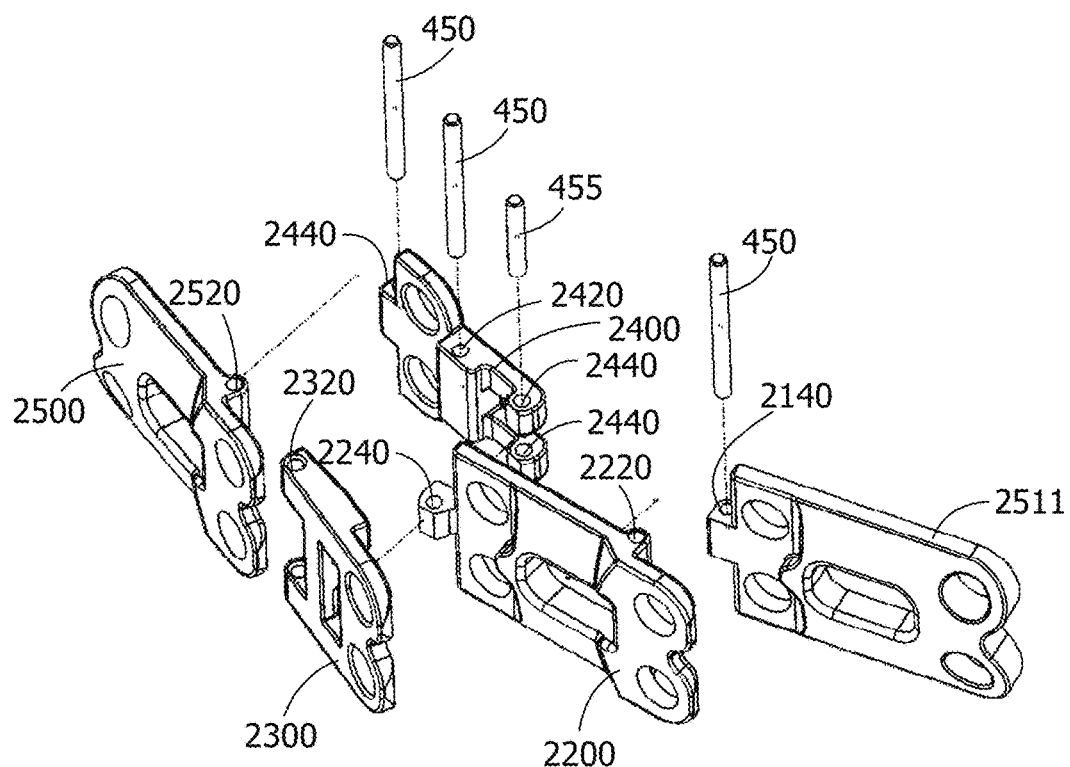
FIG. 27 is an exploded front perspective view of an implantable modular orthopedic plate system according to the disclosure.
Figure 28:
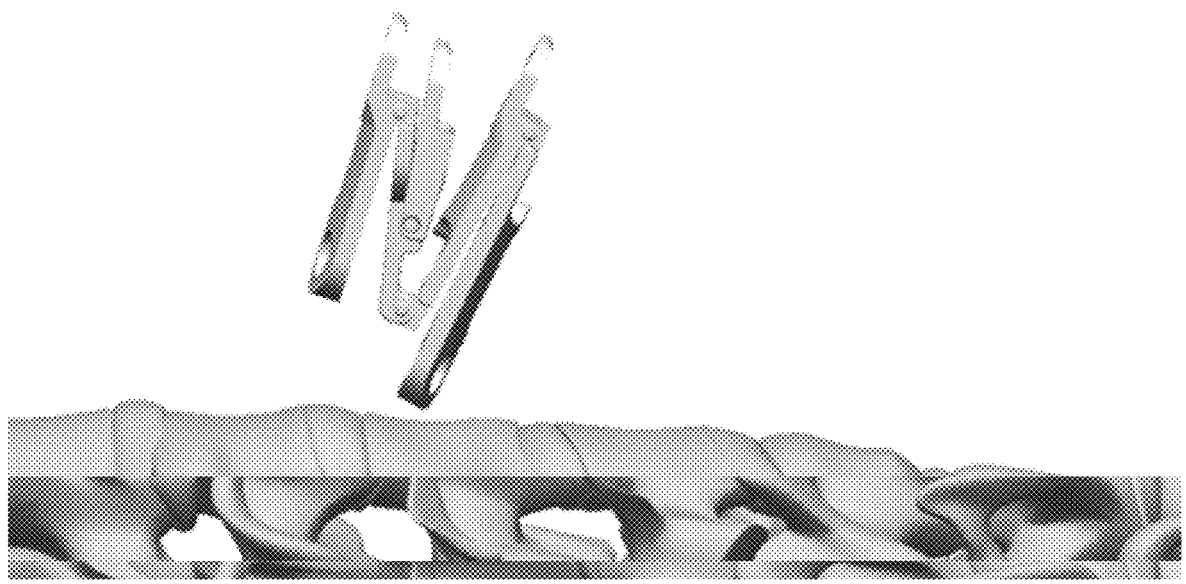
FIG. 28 is a schematic image in a series of images that depict sequential unfolding of an implantable modular orthopedic plate system according to the disclosure.
Figure 29:
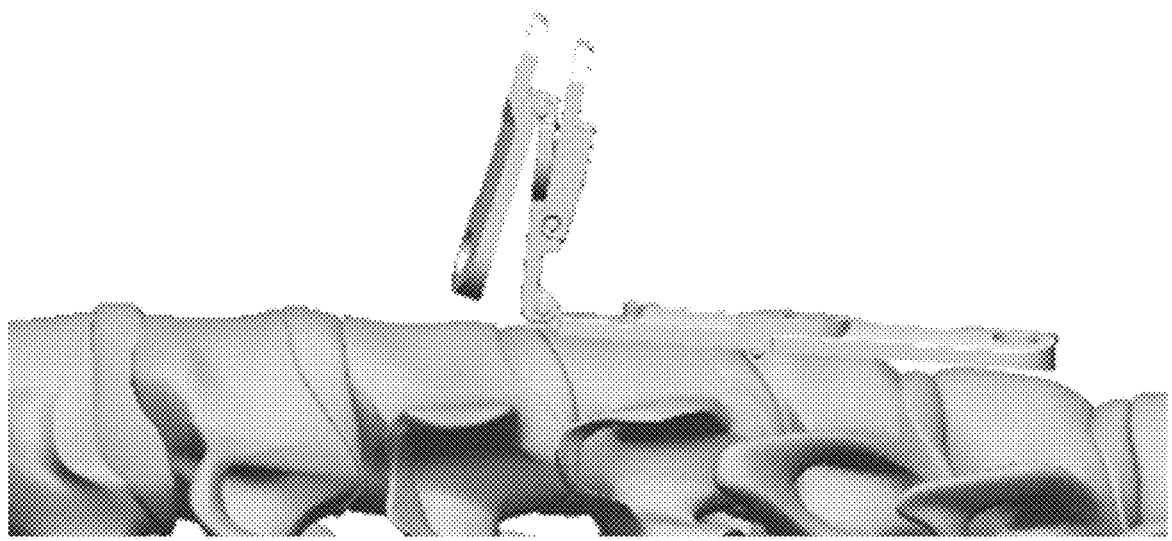
FIG. 29 is a schematic image in a series of images that depict sequential unfolding of an implantable modular orthopedic plate system according to the disclosure.
Figure 30:
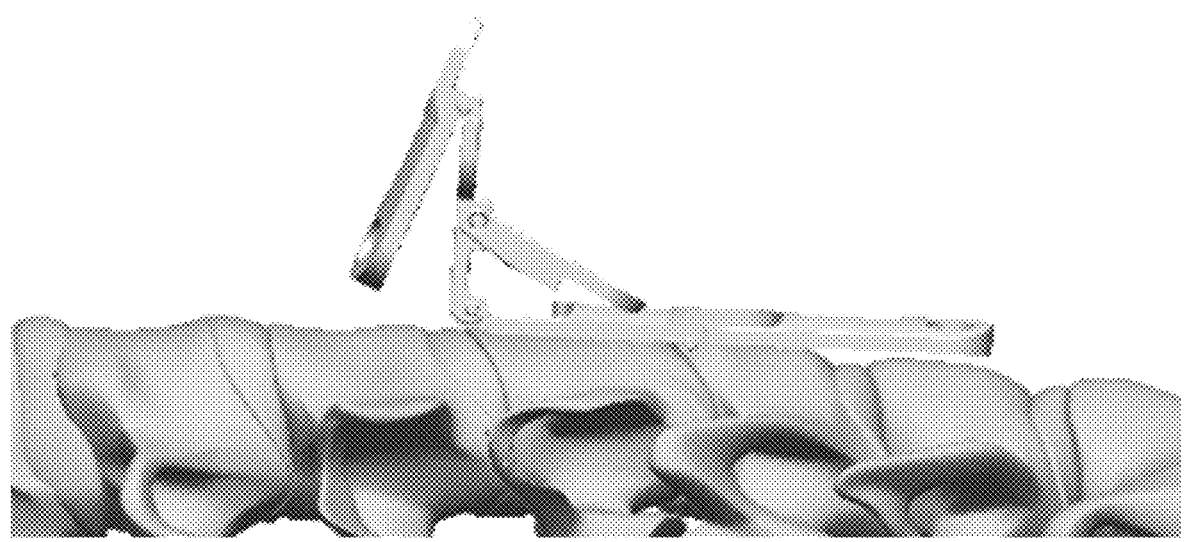
FIG. 30 is a schematic image in a series of images that depict sequential unfolding of an implantable modular orthopedic plate system according to the disclosure.
Figure 31:
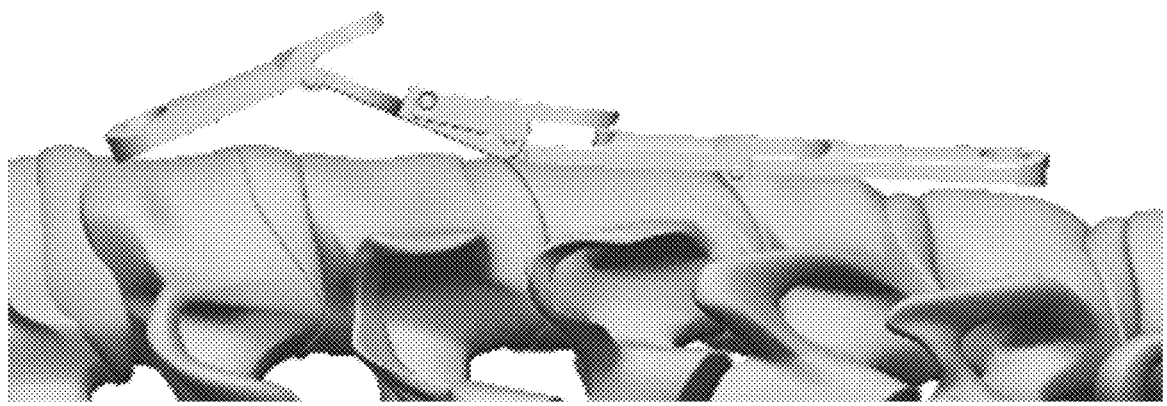
FIG. 31 is a schematic image in a series of images that depict sequential unfolding of an implantable modular orthopedic plate system according to the disclosure.
Figure 32:
FIG. 32 is a schematic image in a series of images that depict sequential unfolding of an implantable modular orthopedic plate system according to the disclosure.

Referring now to FIG. 19, it will be appreciated that the plate segments shown there include several analogous structural features with those described above with respect to the embodiment of the implantable modular orthopedic plate system shown in FIG. 1-FIG. 9. And like the embodiment of the implantable modular orthopedic plate system in FIG. 1-FIG. 9, some of these features may be varied as described above.

Again referring to FIG. 19, another embodiment of an implantable modular orthopedic plate system is shown. Each of FIG. 19-FIG. 27 show alternate views of a multi-level hinged system 2000 according to the disclosure. As shown, the multi-level hinged system 2000 is suitable for use to fix and stabilize four levels (i.e., traversing four disc spaces and engaging with five vertebrae). The multi-level hinged system 2000 includes five plate segments that are interconnectable by connection means that include hinges, tongue in groove engagement, and combinations thereof. Thus, while the drawing show engagement of each segment by hinged connection, that enables the segments to be folded, it will be appreciated that one or more of the segments may be reliably connected to the adjacent plate segment(s). The multi-level system 2000 includes a base plate 2100 that includes an inner digit receiver 2140 for receiving a pin 450, a first extension plate 2200 that includes an outer digit receiver 2220 and an inner digit receiver 2240 each for receiving a pin 450, a second extension plate 2300 that includes an outer digit receiver 2320 for receiving a pin 450, a linker plate 2400 that includes an outer digit receiver 2420 for receiving a pin 450 and an inner digit receiver 2440 for receiving a pin 455, and a terminal extension plate 2500 that includes an outer digit receiver 2520 for receiving a pin 450. Referring now to FIG. 28-FIG. 32, a series of sequential schematic drawings show the multi-level hinged system 2000 as deployed on the anterior surface of a segment of spine, wherein the hinged plate segments are folded into a compact form for insertion into a surgical field and then elongated by unfolding to slide the segments into contact with the spinal bone in a manner that minimizes the force applied to the soft tissue as compared with an inflexible prior art multi-level plate.

While the exemplified multi-level system 2000 includes hinges for connection between the plate segments, it will be appreciated that the hinge pins 450, 455 could be eliminated and the plates engaged via the interdigitating digits such as the ones employed for joining the plate segments with pins, or they may be joined using tongue-in-groove engagements that are either inline or engage via contact between the opposing upper lower surfaces of the plate segments, or they may be aligned without inter-engaging features, such as by employing the shaped/keyed features that are employed on the surfaces of the plate segments as described herein. And in some embodiments, some but not all of the plate segments may be hingedly engaged while others are engaged using an engagement means as described herein or other engagement means that are known in the art and can be reasonably employed for engagement between the plate segments. It should be understood that any movable/hinged engagement between plate segments having a flange/flange recess interface will be limited in their relative motion around the hinge pivot axis PA in view of the interference between the flange and the underlying plate segment.

According to in vitro ASTM tests with a two level modular implant according to the disclosure, as shown in FIG. 1, clinically and commercially significant performance was observed in static and dynamic bend testing, comparable to conventional prior art predicates.

In some embodiments, the disclosure provides a modular plate system for stabilizing adjacent vertebral bodies in a cervical spine, said plate system comprising:

at least two plate segments aligned or connected together so as to form a connection at and along adjacent ends, at least one of the at least two plate segments including a flange at an engagement end and at least one of the at least two plate segments including a flange recess at an engagement end, the flange being configured for overlay engagement with the flange recess when the at least two plate segments are engaged, such that the at least two plate segments are pivotable out of plane with one another at a common axis of rotation traversing overlapping portions of the adjacent ends and are constrained from rotation by the flanges such that the rotation of each plate segment is limited to up to 90 degrees of rotation away from the contact surfaces of the flange and flange recess, and each of the flange and the flange recess comprising at least one securement hole, wherein the flange and flange recess securement holes are aligned when the flange is contacted with the flange recess; an access aperture in each said plate segment arranged and disposed for visualization of an underlying graft site; and a plurality of securement holes through each plate segment for receiving screws inserted therethrough.

In some embodiments, the disclosure provides a hinged plate system for stabilizing adjacent vertebral bodies in a cervical spine, said plate system comprising:

at least two plate segments aligned or connected together so as to form a connection at and along adjacent ends, at least one of the at least two plate segments including a flange at an engagement end and at least one of the at least two plate segments including a flange recess at an engagement end, the flange being configured for overlay engagement with the flange recess when the at least two plate segments are engaged, such that the at least two plate segments are pivotable out of plane with one another at a common axis of rotation traversing overlapping portions of the adjacent ends and are constrained from rotation by the flanges such that the rotation of each plate segment is limited to up to 90 degrees of rotation away from the contact surfaces of the flange and flange recess, and each of the flange and the flange recess comprising at least one securement hole, wherein the flange and flange recess securement holes are aligned when the flange is contacted with the flange recess; an access aperture in each said plate segment arranged and disposed for visualization of an underlying graft site; and a plurality of securement holes through each plate segment for receiving screws inserted therethrough.

In some embodiments, the access aperture is enclosed around its periphery, and includes a size dimension greater than a size dimension of any of the plurality of securement holes.

In some embodiments, the folding plate system includes a hinged connection that comprises a pair of support arms extending from one end of a first plate segment of said plate segments, a pivot pin supported by said support arms in spaced relation to said one end, and a receiver bore extending transversely of one end of a second plate segment of said plate segments, said pin being rotatably received in said bore to pivotally connect together said first plate segment and second plate segment, wherein a slot extends longitudinally in said one end of said second plate segment in angularly offset relation below a plane of said second plate segment, said slot opening into said bore and enabling said pivot pin to be inserted endwise into said bore, said slot terminating in spaced relation to an adjacent side edge of said second plate segment, wherein an end of said slot forms a stop that limits how far the pivot pin can be inserted into said bore; and notches formed in said one end of said second plate segment in spaced locations along said one end corresponding to locations of said support arms on said first plate segment when said pivot pin of said first plate segment is fully inserted into the bore of said second plate segment, said notches extending transversely to said slot and terminating at their upper and lower extremities in upper and lower surfaces, respectively, of said second plate segment to enable said plate segments to be pivoted up and down relative to one another.

In some embodiments, the folding plate system includes only said two adjacent plate segments that are hinged together to form a two-level system.

In some embodiments, the folding plate system includes said at least two plate segments comprised of said two adjacent plate segments and an additional plate segment to provide at least three plate segments that are hinged together to form a three-level system.

In some embodiments, the hinged connection comprises a pair of support arms extending from one end of a first plate segment of said plate segments, a pivot pin supported by said support arms in spaced relation to said one end, and a bore extending transversely of one end of a second plate segment of said plate segments, said pin being rotatably received in said bore to pivotally connect together said first plate segment and second plate segment, wherein a slot extends longitudinally in said one end of said second plate segment in angularly offset relation below a plane of said second plate segment, said slot opening into said bore and enabling said pivot pin to be inserted endwise into said bore, said slot terminating in spaced relation to an adjacent side edge of said second plate segment, wherein an end of said slot forms a stop that limits how far the pivot pin can be inserted into said bore; and notches formed in said one end of said second plate segment in spaced locations along said one end corresponding to locations of said support arms on said first plate segment when said pivot pin of said first plate segment is fully inserted into the bore of said second plate segment, said notches extending transversely to said slot and terminating at their upper and lower extremities in upper and lower surfaces, respectively, of said second plate segment to enable said plate segments to be pivoted up and down relative to one another.

In some embodiments, at least two plate segments of the folding plate system are hingedly connected together and are arranged and disposed to hinge for pivoting movement through at least 90° in each of two directions relative to one another.

In some embodiments, at least two plate segments of the folding plate system are hingedly connected together and are arranged and disposed to hinge for pivoting movement wherein they are constrained from rotation by the flanges such that the rotation of each plate segment is limited to up to 90 degrees of rotation away from the contact surfaces of the flange and flange recess.

In some embodiments of the folding plate system at least one of the plate segments includes an end opposite the hingedly connected adjacent ends which is free of a hinge-forming structure.

In some embodiments of the folding plate system the plurality of securement holes through each plate segment includes four securement holes through each plate segment.

In some embodiments of the folding plate system the four securement holes are disposed adjacent to four corners of each plate segment.

In some embodiments of the folding plate system the access aperture is disposed at a center of each plate segment.

In some embodiments of the folding plate system each of the plate segments includes an end opposite hingedly connected adjacent ends which includes a hinge-forming structure or is free of a hinge-forming structure, the access aperture is enclosed around its periphery, and the access aperture includes a size dimension greater than a size dimension of any of the plurality of securement holes.

As used herein, the singular forms "a," "an," and "the" are intended to include the plural forms as well, unless the context clearly indicates otherwise. The term "proximal" as used in connection with any object refers to the portion of the object that is closest to the operator of the object (or some other stated reference point), and the term "distal" refers to the portion of the object that is farthest from the operator of the object (or some other stated reference point). The term "operator" means and refers to any professional or paraprofessional who delivers clinical care to a medical patient, particularly in connection with the delivery of care.

Anatomical references as used herein are intended to have the standard meaning for such terms as understood in the medical community. For example, the application may include reference to the following terms: "cephalad," "cranial" and "superior" indicate a direction toward the head, and the terms "caudad" and "inferior" indicate a direction toward the feet. Likewise, the terms "dorsal" and "posterior" indicate a direction toward the back, and the terms "ventral" and "anterior" indicate a direction toward the front. And the term "lateral" indicates a direction toward a side of the patient. The term "medial" indicates a direction toward the mid line of the patient, and away from the side, the term "ipsilateral" indicates a direction toward a side that is proximal to the operator or the object being referenced, and the term "contralateral" indicates a direction toward a side that is distal to the operator or the object being referenced.

Unless otherwise indicated, all numbers expressing quantities, properties, and so forth as used in the specification, drawings and claims are to be understood as being modified in all instances by the term "about." Accordingly, unless otherwise indicated, the numerical properties set forth in the specification and claims are approximations that may vary depending on the suitable properties desired in embodiments of the present invention. Notwithstanding that the numerical ranges and parameters setting forth the broad scope of the general inventive concepts are approximations, the numerical values set forth in the specific examples are reported as precisely as possible. Any numerical values, however, inherently contain certain errors necessarily resulting from error found in their respective measurements.

One of ordinary skill will appreciate that references to positions in the body are merely representative for a particular surgical approach. Further, all references herein are made in the context of the representative images shown in the drawings. Fewer or additional instruments, including generic instruments, may be used according to the preference of the operator. Moreover, references herein to specific instruments are not intended to be limiting in terms of the options for use of other instruments where generic options are available, or according to the preference of the operator.

While the disclosed embodiments have been described and depicted in the drawings in the context of the human spine, it should be understood by one of ordinary skill that all or various aspects of the embodiments hereof may be used in connection with other species and within any species on other parts of the body.

While various inventive aspects, concepts and features of the general inventive concepts are described and illustrated herein in the context of various exemplary embodiments, these various aspects, concepts and features may be used in many alternative embodiments, either individually or in various combinations and sub-combinations thereof. Unless expressly excluded herein all such combinations and sub-combinations are intended to be within the scope of the general inventive concepts. Still further, while various alternative embodiments as to the various aspects, concepts and features of the inventions (such as alternative materials, structures, configurations, methods, devices and components, alternatives as to form, fit and function, and so on) may be described herein, such descriptions are not intended to be a complete or exhaustive list of available alternative embodiments, whether presently known or later developed.

Those skilled in the art may readily adopt one or more of the inventive aspects, concepts and features into additional embodiments and uses within the scope of the general inventive concepts, even if such embodiments are not expressly disclosed herein. Additionally, even though some features, concepts and aspects of the inventions may be described herein as being a preferred arrangement or method, such description is not intended to suggest that such feature is required or necessary unless expressly so stated. Still further, exemplary or representative values and ranges may be included to assist in understanding the present disclosure; however, such values and ranges are not to be construed in a limiting sense and are intended to be critical values or ranges only if so expressly stated.

Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order that the steps are presented to be construed as required or necessary unless expressly so stated.

What is claimed is:

1. An implantable modular orthopedic plate system, comprising:
   at least two plate segments, each plate segment including a top surface, a bottom surface, and first and second ends, wherein at least one end of each of the plate segments is an engagement end for engagement with an adjacent plate segment, the plate segments being connectible together at and along adjacent engagement ends,
   an access aperture in each of the at least two plate segments, each access aperture arranged and disposed for visualization through the plate segment;
   a plurality of securement holes through each of the at least two plate segments for receiving screws inserted therethrough; and
   at least one of the at least two plate segments including at its engagement end a flange suitable for overlay engagement with a flange recess on the engagement end of an adjacent plate segment, each of the flange and the flange recess comprising a plurality of securement holes, wherein the plurality of securement holes are aligned when the flange is contacted with the flange recess, and wherein the plate segments are configured to be fixed together to a bone once implanted by passage of screws through the aligned plurality of securement holes of the flange and the flange recess to provide a secured and reinforced interface between the at least two plate segments and against the bone.

2. The implantable modular orthopedic plate system as claimed in claim 1, wherein the at least two plate segments are either fixedly connected together or are releasably connectible together.

3. The implantable modular orthopedic plate system as claimed in claim 2, wherein the at least two plate segments are hingedly connectible such that the plate segments are pivotable out of plane with one another, a pivot motion of each plate being about 180 degrees around the pivot axis, subject to any restricted motion due to interference between the flange and the flange recess.

4. The implantable modular orthopedic plate system as claimed in claim 3, wherein the at least two plate segments are connected together with a fixed hinge, the fixed hinge comprising one or a plurality of receiving channels on each of the engagement ends of the plate segments, and an engagement pin for fixing them together.

5. The implantable modular orthopedic plate system as claimed in claim 3, wherein the at least two plate segments are connected together with a releasable hinge, the releasable hinge comprising one or a plurality of engagable arcuate flanges on each of the engagement ends of each of the plate segments, the arcuate flanges adapted for engagement to form a pivot axis.

6. The implantable modular orthopedic plate system as claimed in claim 1, wherein the at least two plate segments are sized for attachment to and stabilizing adjacent vertebrae in a cervical spine.

7. The implantable modular orthopedic plate system as claimed in claim 1, wherein the at least two plate segments comprise only the two adjacent plate segments that are connectible together to form a two-level system.

8. The implantable modular orthopedic plate system as claimed in claim 1, wherein at least one of the at least two plate segments comprises another engagement end that comprises one of a flange or a flange recess.

9. The implantable modular orthopedic plate system as claimed in claim 1, wherein at least two of the at least two plate segments comprises another engagement end that comprises one of a flange or a flange recess.

10. The implantable modular orthopedic plate system as claimed in claim 1, wherein the at least two plate segments comprise the two adjacent plate segments and an additional plate segment to provide at least three plate segments that are connectible to form a three-level system.

11. The implantable modular orthopedic plate system as claimed in claim 1, comprising at least three plate segments, wherein at least two of the plate segments comprise two engagement ends, each of which engagement ends comprises one of a flange or a flange recess, the at least three plate segments connectible to form a three-level system.

12. The implantable modular orthopedic plate system as claimed in claim 1, comprising at least three plate segments, wherein each of the at least three plate segments comprise two engagement ends, and at least one of the engagement ends on at least two of the at least three plate segments comprises one of a flange or a flange recess, the at least three plate segments connectible to form at least a three-level system.

13. The implantable modular orthopedic plate system as claimed in claim 1, wherein at least one of the at least two plate segments includes an end opposite the engagement end which is free from any engagement feature.

14. The implantable modular orthopedic plate system as claimed in claim 1, wherein the plurality of securement holes through each of the at least two plate segments includes four securement holes through each plate segment.

15. The implantable modular orthopedic plate system as claimed in claim 14, wherein the four securement holes are disposed adjacent to four corners of each plate segment.

16. The implantable modular orthopedic plate system as claimed in claim 1, wherein the access aperture is disposed at a center of each plate segment.

17. The implantable modular orthopedic plate system as claimed in claim 1, wherein each plate segment has one or more of a thickness dimension in a range from about 1 to about 10 mm, a width dimension in a range from about 10 to about 60 mm, and a length dimension in a range from about 10 to about 100 mm.

18. The implantable modular orthopedic plate system as claimed in claim 1, wherein each plate segment has one or more of a thickness dimension in a range from about 2 to about 3 mm, a width dimension in a range from about 6 to about 10 mm, and a length dimension in a range from about 20 to about 30 mm.

19. An implantable modular plate system for stabilizing adjacent vertebral bodies in a cervical spine, comprising:
at least two plate segments aligned or connected together so as to form a connection at and along adjacent ends, at least one of the at least two plate segments including a flange at an engagement end and at least one of the at least two plate segments including a flange recess at an engagement end, the flange being configured for overlay engagement with the flange recess when the at least two plate segments are engaged, such that the at least two plate segments are pivotable out of plane with one another at a common axis of rotation traversing overlapping portions of the adjacent ends and are constrained from rotation by the flanges and the flange recess such that rotation of each plate segment is limited to up to 90 degrees of rotation away from contact surfaces of the flange and flange recess, and each of the flange and the flange recess comprising at least one securement hole, wherein the flange and flange recess securement holes are aligned when the flange is contacted with the flange recess;
an access aperture in each plate segment arranged and disposed for visualization of an underlying graft site; and
a plurality of securement holes through each plate segment for receiving screws inserted therethrough.

20. An implantable modular orthopedic plate system, comprising:
at least two plate segments, each plate segment including a top surface, a bottom surface, and first and second ends, the plate segments being connectible together at and along adjacent engagement ends, wherein each of the at least two plate segments comprises two engagement ends, each engagement end for engagement with an engagement end of an adjacent plate segment, wherein at least one of the engagement ends on at least two of the at least two plate segments comprises one of a flange, or a flange recess;
an access aperture in each of the at least two plate segments, each access aperture arranged and disposed for visualization through the plate segment; and
a plurality of securement holes through each of the at least two plate segments for receiving screws inserted therethrough; and
at least one of the at least two plate segments including at an engagement end a flange that is oriented adjacent to another of the at least two plate segments including a flange recess at its adjacent engagement end, each of the flange and the flange recess comprising a plurality of securement holes, wherein the plurality of securement holes are aligned when the flange is contacted with the flange recess, and wherein the plate segments are configured to be fixed together to a bone once implanted by passage of screws through the aligned plurality of securement holes of the flange and the flange recess to provide a secured and reinforced interface between the at least two plate segments and against the bone.

\* \* \* \* \*